United States Patent
Hoshino et al.

(10) Patent No.: US 10,060,997 B2
(45) Date of Patent: Aug. 28, 2018

(54) MAGNETIC RESONANCE IMAGING APPARATUS AND OPERATING METHOD OF COOLING FAN MOTOR OF MAGNETIC RESONANCE IMAGING APPARATUS

(71) Applicant: HITACHI, LTD., Tokyo (JP)

(72) Inventors: Shin Hoshino, Tokyo (JP); Kenji Sakakibara, Tokyo (JP)

(73) Assignee: HITACHI, LTD., Tokyo (JP)

( * ) Notice: Subject to any disclaimer, the term of this patent is extended or adjusted under 35 U.S.C. 154(b) by 677 days.

(21) Appl. No.: 14/441,914

(22) PCT Filed: Dec. 2, 2013

(86) PCT No.: PCT/JP2013/082316
§ 371 (c)(1),
(2) Date: May 11, 2015

(87) PCT Pub. No.: WO2014/087954
PCT Pub. Date: Jun. 12, 2014

(65) Prior Publication Data
US 2015/0301134 A1    Oct. 22, 2015

(30) Foreign Application Priority Data
Dec. 5, 2012   (JP) .................................. 2012-266128

(51) Int. Cl.
*G01R 33/385*   (2006.01)
*G01R 33/30*    (2006.01)
(Continued)

(52) U.S. Cl.
CPC ....... *G01R 33/3856* (2013.01); *G01R 33/307* (2013.01); *G01R 33/31* (2013.01);
(Continued)

(58) Field of Classification Search
CPC ............ G01R 33/3856; G01R 33/3815; G01R 33/3403; A61B 5/055
(Continued)

(56) References Cited

U.S. PATENT DOCUMENTS

| 5,838,085 A | * | 11/1998 | Roesel, Jr. ............... F02N 11/04 310/112 |
| 2012/0249134 A1 | | 10/2012 | Rapoport et al. |
| 2013/0002230 A1 | * | 1/2013 | Starkweather, Sr. ... H02M 1/36 323/321 |

FOREIGN PATENT DOCUMENTS

| JP | H01-145050 A | 6/1989 |
| JP | H02-237541 A | 9/1990 |

(Continued)

OTHER PUBLICATIONS

Feb. 25, 2014 Search Report issued in International Patent Application No. PCT/JP2013/082316.

*Primary Examiner* — Melissa Koval
*Assistant Examiner* — Courtney McDonnough
(74) *Attorney, Agent, or Firm* — Oliff PLC

(57) ABSTRACT

To prevent image quality deterioration of an image due to a variable magnetic field generated by a fan motor provided in a position where a measuring magnetic field leaks, a magnetic resonance imaging apparatus has a gantry including a static magnetic field generating magnet; a gradient magnetic field generating coil; and an irradiation coil, a table for placing the object, and an input/output device including a display device and is provided with at least a pair of cooling fan motors arranged almost symmetrically to the central axis that extends along the long-axis direction of the cylindrical space and is located in the center in the horizontal direction of the static magnetic field generating magnet or the vertical plane passing through the central axis.

5 Claims, 16 Drawing Sheets

(51) Int. Cl.
  *G01R 33/3815* (2006.01)
  *G01R 33/31* (2006.01)
  *G01R 33/34* (2006.01)
  *G01R 33/565* (2006.01)
  *A61B 5/055* (2006.01)
(52) U.S. Cl.
  CPC ..... *G01R 33/3403* (2013.01); *G01R 33/3815* (2013.01); *G01R 33/56563* (2013.01); *A61B 5/055* (2013.01)
(58) Field of Classification Search
  USPC .................................................. 324/307, 321
  See application file for complete search history.

(56) References Cited

FOREIGN PATENT DOCUMENTS

| | | |
|---|---|---|
| JP | H08-98828 A | 4/1996 |
| JP | 2011-143160 A | 7/2011 |
| JP | 2012-026973 A | 2/2012 |
| JP | 3178147 U | 9/2012 |

\* cited by examiner

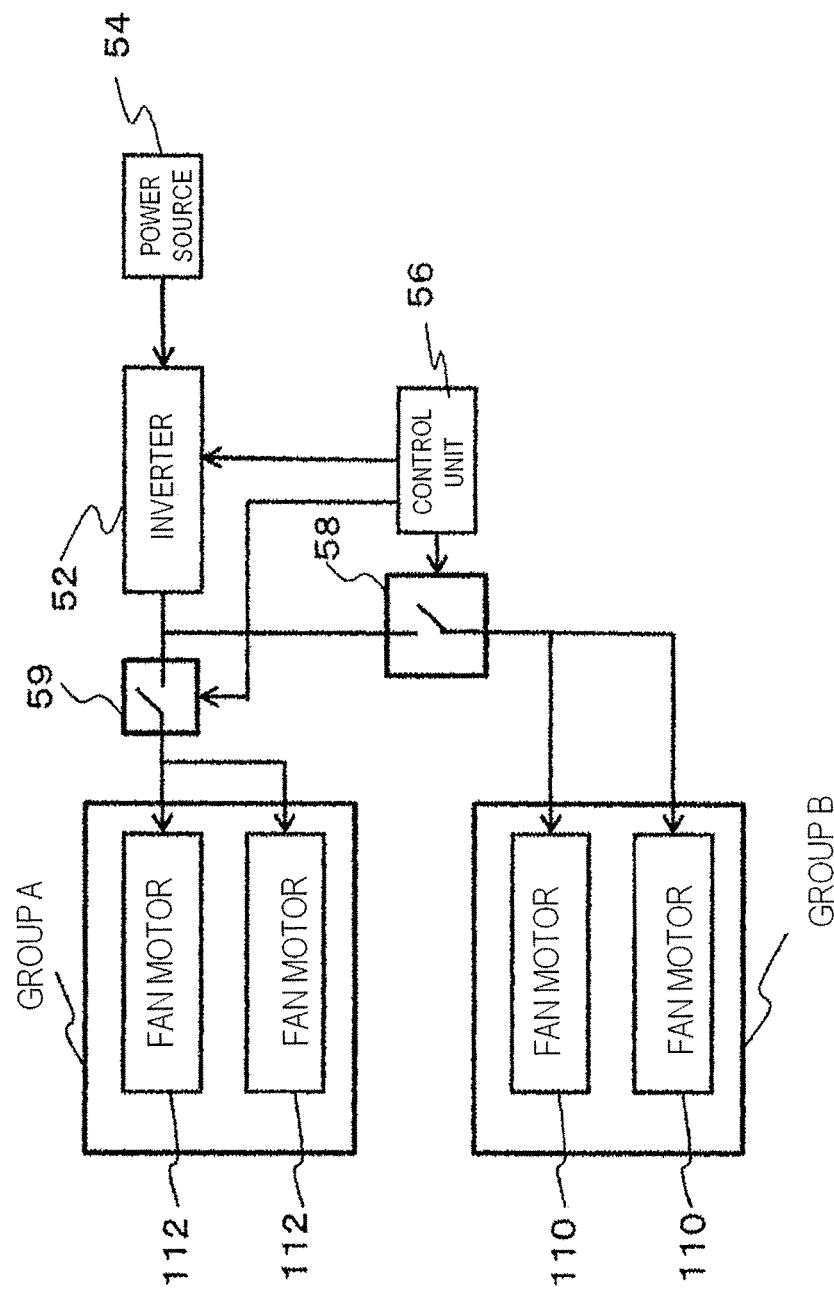

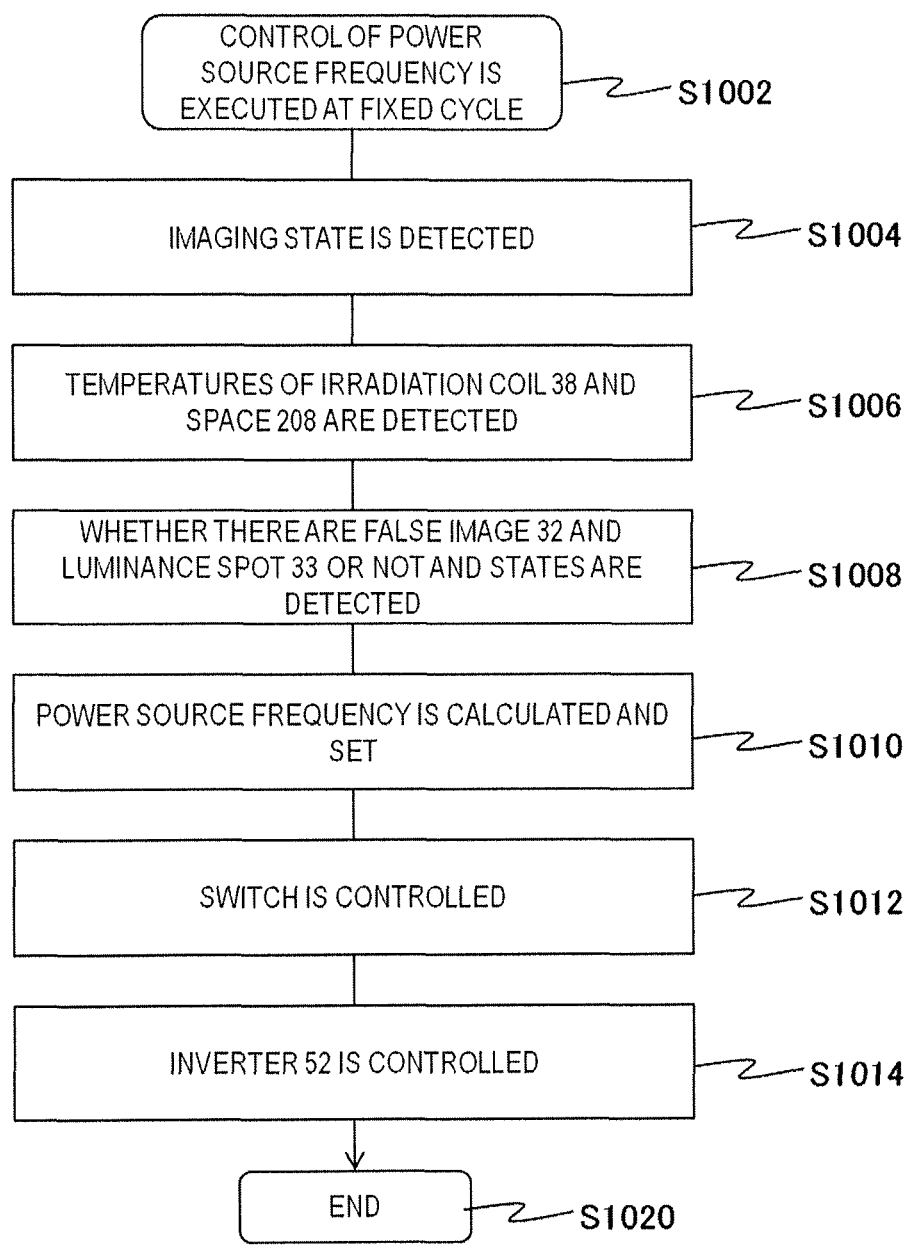

MAGNETIC RESONANCE IMAGING APPARATUS AND OPERATING METHOD OF COOLING FAN MOTOR OF MAGNETIC RESONANCE IMAGING APPARATUS

TECHNICAL FIELD

The present invention relates to a magnetic resonance imaging apparatus and in particular to a magnetic resonance imaging apparatus provided with a cooling fan motor.

BACKGROUND ART

A magnetic resonance imaging (hereinafter, referred to as MRI) apparatus is an apparatus that measures a signal sent from a desired examination site of an object using the nuclear magnetic resonance (hereinafter, referred to as NMR) phenomenon and displays an image by changing density distribution and relaxation time distribution of nuclear spin in the examination site to a tomographic image etc.

In a conventional MRI apparatus, for example, a space forming a measurement area for measuring an object is formed in the center of the gantry in a horizontal superconducting magnetic field generating device, and an irradiation coil, a gradient magnetic field coil, a static magnetic field generating device, etc. are arranged outside the space.

An MRI apparatus has been highly functional in the recent years. Accordingly, the irradiation coil is heavily loaded, and the heat generation amount tends to increase. An air-cooling fan is used to cool the irradiation coil. An example of an MRI apparatus provided with such an air-cooling fan is described in (Patent Literature 1)

CITATION LIST

Patent Literature

PTL 1: Japanese Patent Application Publication No. 2011-143160

SUMMARY OF INVENTION

Technical Problem

It has been expected that an MRI apparatus should be more highly functional as described above, and it has been more important to improve magnetic field quality in a measurement area. Since a fan motor has the structure where a rotational torque is generated by generating a magnetic field, the magnetic field generated by the fan motor cannot be ignored for image quality deterioration of an MRI apparatus.

In the PTL 1, a cooling fan is arranged in a position very distant from a cooling target, such as a protruding position from an outer cover of an MRI apparatus. Additionally, in FIG. 8 etc. of PTL 1, the outer cover is extended, and the cooling fan is arranged on the outer peripheral part on the ceiling side of the outer cover. In this case, the outer cover is extended so that a helium cooling freezer is covered. Thus, although a magnetic influence by the fan can be reduced when the fan is arranged in a position very distant from a measurement space of the MRI apparatus, this results in that the fan is very distant from a part to be cooled.

A fan motor should not be arranged in a position very distant from a magnetic field generating device of an MRI apparatus, but it is desirable that an influence of the fan motor against measurement of the MRI apparatus can be reduced despite that the fan motor is arranged in a position where a measuring magnetic field of the MRI apparatus leaks. In other words, it is desirable that a measured image can be prevented from image quality deterioration by the fan motor despite that the fan motor is arranged in a position where a measuring magnetic field of the MRI apparatus leaks.

The purpose of the present invention is to provide an MRI apparatus and the operating methods of the cooling fan motor that can reduce an influence of variable magnetic fields generated by the fan motor and prevent image quality deterioration.

Solution to Problem

In order to solve the above problems, the first invention provides a magnetic resonance imaging apparatus that has a gantry including a static magnetic field generating magnet that has a cylindrical space to accommodate an object and generates a static magnetic field in the said space, a gradient magnetic field generating coil that generates a gradient magnetic field, and an irradiation coil that irradiates a high-frequency signal; a table for placing the object; and an input/output device including a display device and that is provided with at least a pair of cooling fan motors arranged almost symmetrically to the central axis that extends along the long-axis direction of the cylindrical space and is located in the center in the horizontal direction of the static magnetic field generating magnet or the vertical plane passing through the said central axis.

In order to solve the above problems, the other invention provides operation methods of cooling fan motors such as starting and stopping a pair of the cooling fan motors of a magnetic resonance imaging apparatus that has a gantry including a static magnetic field generating magnet having a cylindrical space to accommodate an object to generate a static magnetic field in the said space, a gradient magnetic field generating coil generating a gradient magnetic field, and an irradiation coil irradiating a high-frequency signal; a table for placing the object; and an input/output device including a display device and that is provided with at least a pair of cooling fan motors arranged almost symmetrically to the central axis that extends along the long-axis direction of the cylindrical space and is located in the center in the horizontal direction of the static magnetic field generating magnet or the vertical plane passing through the said central axis.

Advantageous Effects of Invention

The present invention can reduce an influence of variable magnetic fields generated by the fan motor and provide an MRI apparatus that can prevent image quality deterioration despite that the fan motor is arranged in a position where a magnetic field of a magnetic field generating device leaks.

BRIEF DESCRIPTION OF DRAWINGS

FIG. 15 is a configuration block diagram for changing a drive frequency of the fan motors.

FIG. 16 is a flow chart for controlling an AC power generating inverter and an AC supply switch.

DESCRIPTION OF EMBODIMENTS

Hereinafter, the embodiments of the present invention will be described based on the diagrams. Additionally, in all the diagrams for explaining the invention embodiments, the same symbols are used for the same functions, and the repeated descriptions will be omitted.

Figure 1:
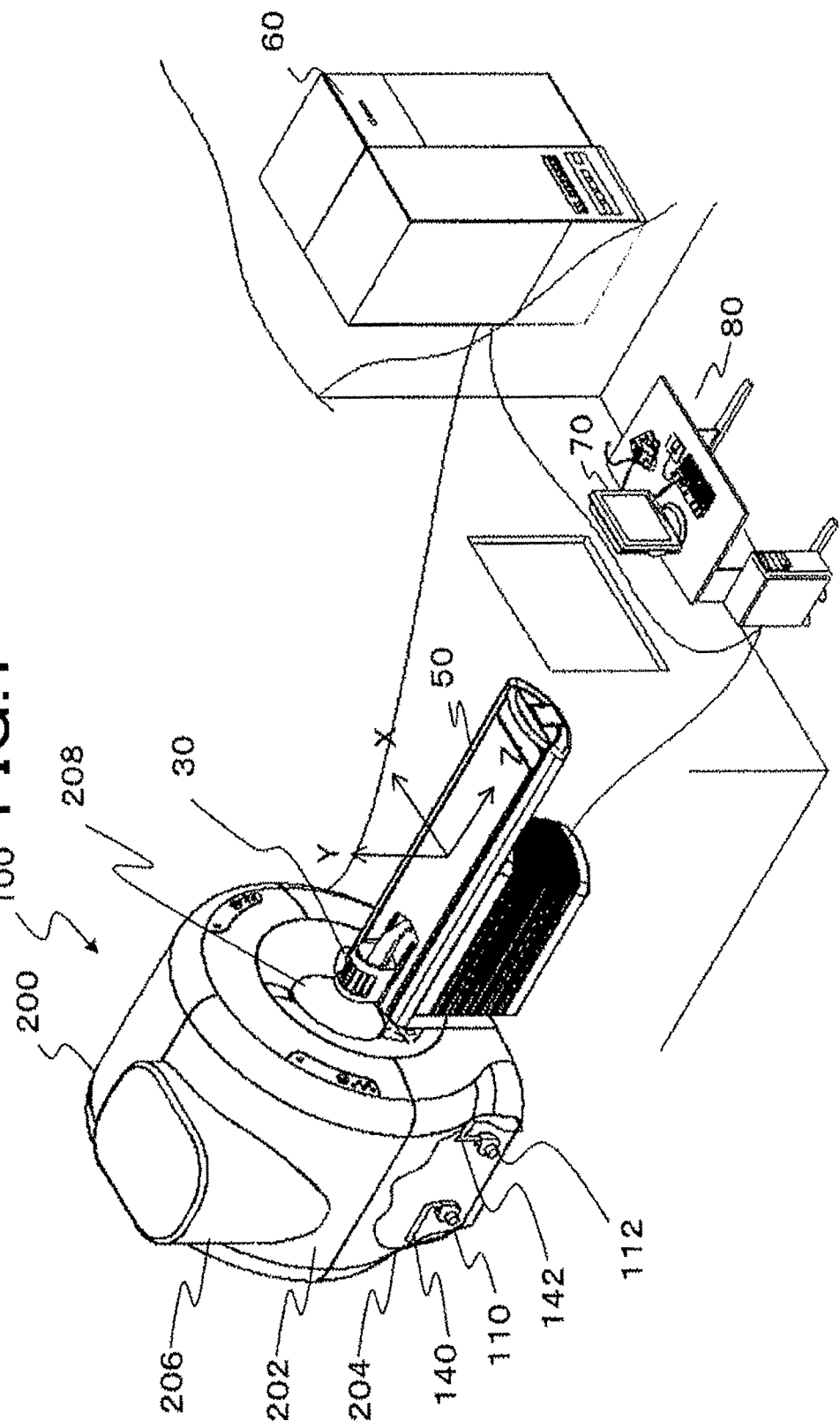
FIG. 1 is an overall perspective diagram of a magnetic resonance imaging apparatus of an example embodiment of the present invention.

FIG. 1 is an overall perspective diagram of an example of a magnetic resonance imaging apparatus related to the present invention. The MRI apparatus 100 has the gantry 200 having the space 208 to accommodate an object in the center, the receiver 30 receiving a signal generated from an examination site of the object based on the NMR phenomenon, the control processor 60 controlling measuring devices provided with the gantry 200 as well as forming an image such as a tomographic image of the examination site based on the signal received by the receiver 30, the table 50 placing the object, and the input/output device 80. The input/output device 80 has the display device 70, the display device 70 displays a tomographic image reconstructed by the control processor 60 as well as the other required information.

The gantry 200 has the superconducting coil, the gradient magnetic field coil, as well as the irradiation coil and creates a measuring space that can use the NMR phenomenon in the space 208. An object placed on the table 50 is sent into the space 208, a measuring magnetic field is generated by the superconducting coil and the gradient magnetic field coil provided in the gantry 200, a high-frequency signal is applied to an examination site of the object from an irradiation coil to receive a signal from the examination site based on the NMR phenomenon with the receiver 30, the control processor 60 reconstructs a tomographic image of the examination site based on the received signal, and then the tomographic image is displayed in the display device 70 of the input/output device 80.

The outermost portion of the gantry 200 is covered with the cover 202. The cover 202 is provided for appearance and safety. Inside the cover 202, the superconducting coil, the gradient magnetic field coil, and the irradiation coil are arranged. These coils will be described in FIG. 4. The receiver 30 receives a signal that an object generates by nuclear magnetic resonance. The table 50 is arranged in a position adjacent to the gantry 200. An object is placed on the table 50 outside the gantry 200, and the table 50 carries the object into the measuring space with the receiver 30 attached on a site to be examined. The control processor 60 performs calculation for image reconstruction using a signal detected by the receiver 30, the constructed image is displayed in the display device 70 provided in the input/output device 80 or is stored in a storage device that is not shown in the diagrams.

In the present embodiment, the following will be described by setting the longitudinal direction of the space 208 as the Z axis, the horizontal direction as the X axis, and the vertical direction as the Y axis. The gantry 200 and the table 50 are arranged in the MRI examination room, and the input/output device 80 for operation and the control processor 60 for control and various processes are arranged outside through a room partition.

Figure 5:
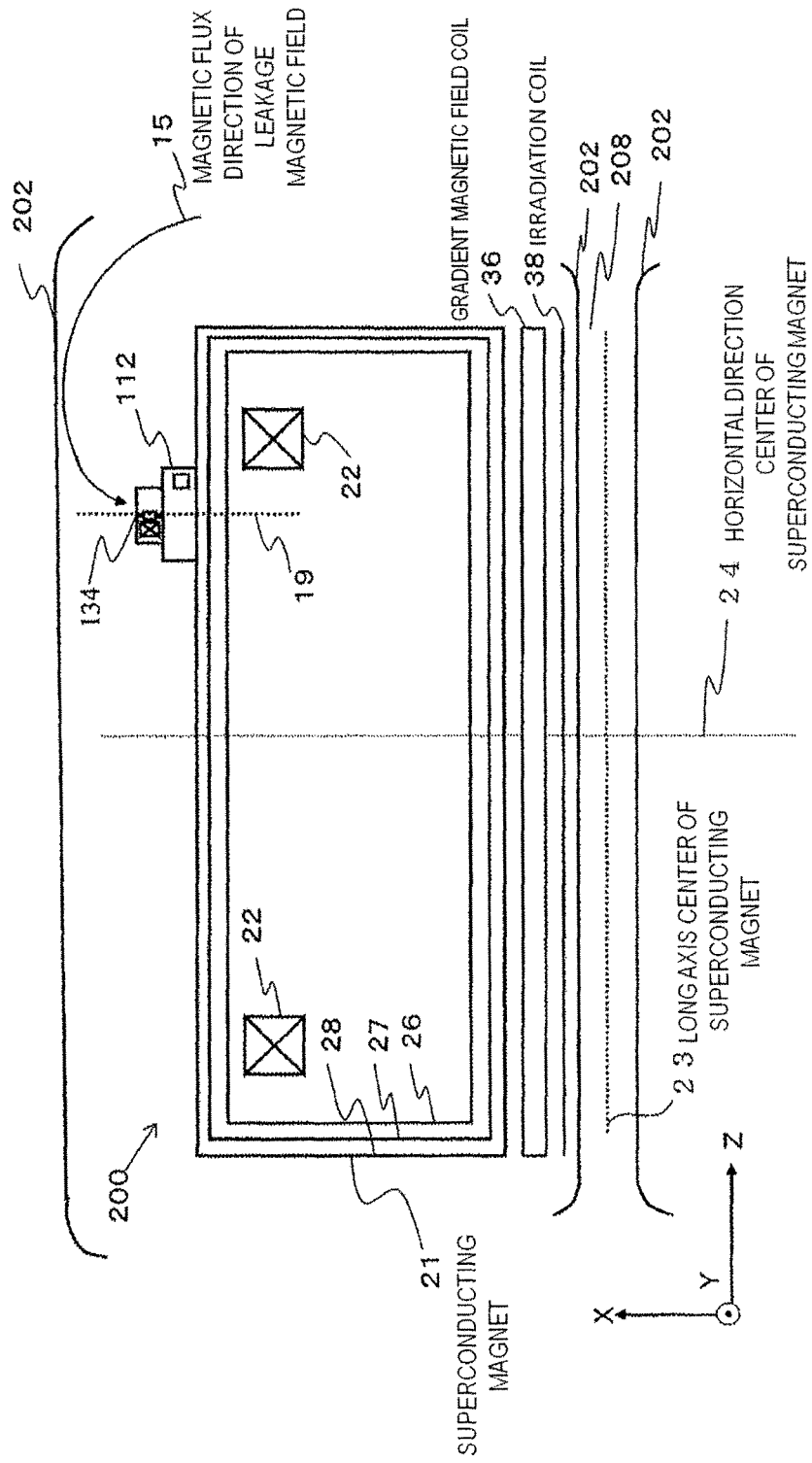
FIG. 5 is an explanatory diagram explaining the relationship between the leakage magnetic flux of the superconducting magnet and the orientation of the fan motor.
Figure 6:
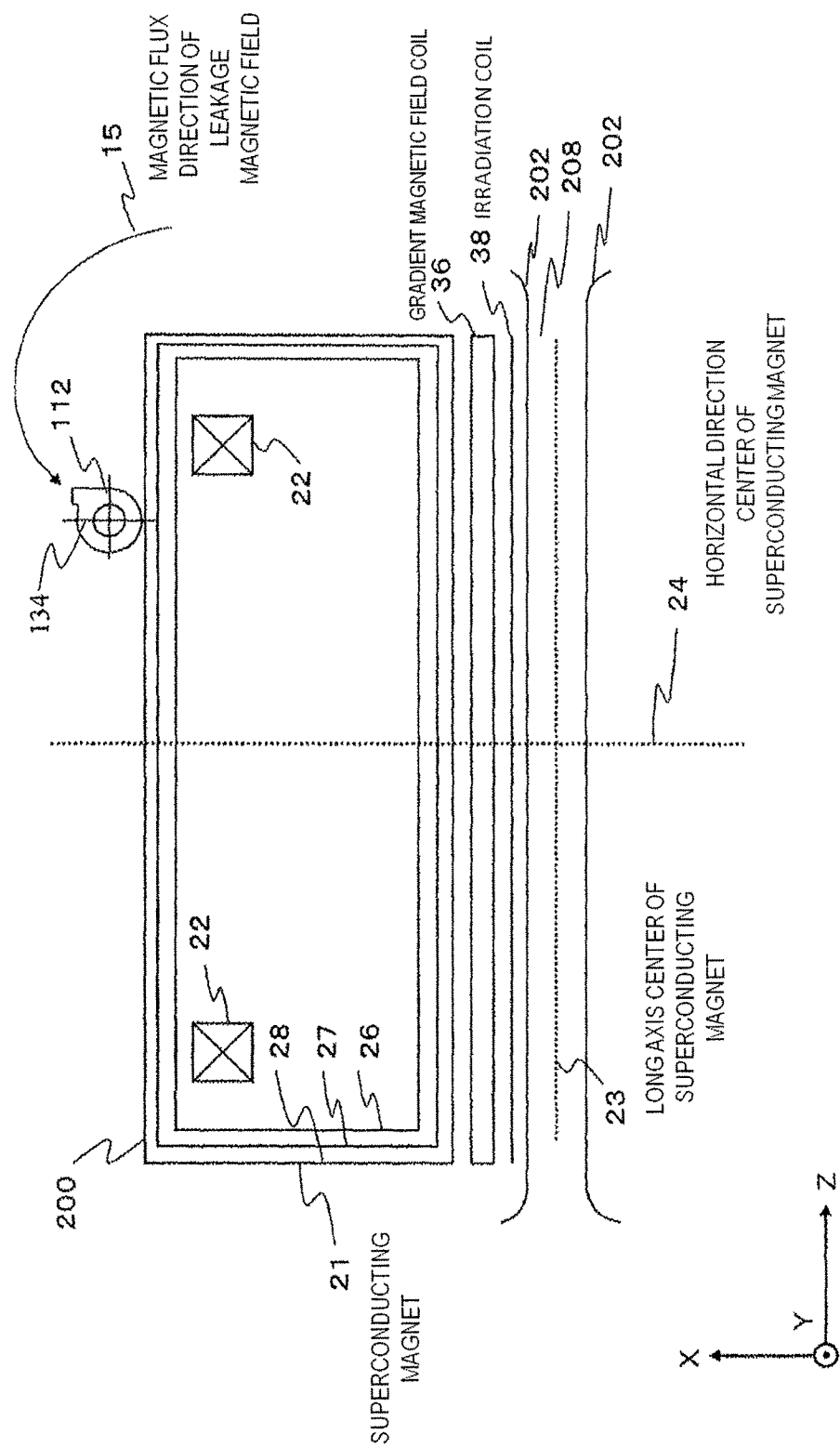
FIG. 6 is a diagram showing the other orientation and position of the fan motor on the superconducting magnet.

An example of arrangement relationship of a superconducting coil, a gradient magnetic field coil, and an irradiation coil inside the gantry 200 is described in FIGS. 5 and 6, and although FIGS. 5 and 6 will be described in detail hereinafter, the arrangement relationship of the superconducting coil 22, the gradient magnetic field coil 36, and the irradiation coil 38 is described using these diagrams in this section. FIGS. 5 and 6 are a part of the cross section along the Z axis, i.e. the longitudinal central axis 23 direction of the superconducting magnet that is the central axis in the longitudinal direction of the space 208 and along the X axis that is the horizontal plane additionally. The space 208 is formed inside the cover 202, the irradiation coil 38 irradiating a high-frequency signal to an examination site of an object is arranged outside the space 208, the gradient magnetic field coil 36 generating a gradient magnetic field is arranged outside the irradiation coil 38, and the superconducting magnet 21 is arranged on the outer side.

The superconducting magnet 21 has the helium vessel 26 having a plurality of the superconducting coils 22, the radiation shield 27, and the vacuum vessel 28. Liquid helium is filled in the helium vessel 26 in order to maintain a superconducting state by cooling the superconducting coils 22, and a freezer is installed inside the cover 206 protruding upward from the cover 202 as shown in FIG. 1 in order to keep the liquid helium in a low temperature. In the present embodiment, because the cover 206 of the gantry 200 protrudes, the cover 202 can be installed in the vicinity of the outer periphery of the superconducting magnet 21 and has an almost circular arc shape that is formed so as to be along the outer periphery of the superconducting magnet 21.

Because a large amount of electric current continues to flow to the irradiation coil 38 adjacent to an object while the MRI apparatus is operating, the irradiation coil 38 generates heat. The IEC regulation regulates that an object contact part should be kept 41 degrees Celsius or less, and an air-cooling unit is provided to cool the irradiation coil 38 in the present embodiment. Alternatively, the air around the object is heated due to its own heat generation because the object is accommodated in the small space 208 for a long time, which may result in that the heated air is accumulated around the object. The object is exposed to a high frequency for long-time imaging. Therefore, a temperature of the object increases slightly. These make the object feel discomfort. In the present embodiment, a plurality of cooling units are provided to cool the irradiation coil 38 as well as the object, which alleviates the object's discomfort.

These multiple air-cooling units are arranged in the space of the gantry 200 and cool not only the space 208 to accommodate an object but also the irradiation coil 38. In FIG. 1, the portion 204 in which the cover 202 is removed is especially described in a part of the cover 202 so that a plurality of the fan motors 110 and 112 as well as a plurality of the duct 140 or 142 can be seen. Originally, the portion 204 in which the cover 202 is removed does not exist. Also, although a plurality of the fan motors 110 and 112 as well as a plurality of the duct 140 or 142 are provided in the opposite side across the space 208, they are on the back side of the gantry 200 and do not appear in FIG. 1. In the present embodiment, because the fan motor 110 or 112 is arranged in the vicinity of the superconducting magnet 21 in the cover 202 of the gantry 200 as shown in FIG. 5, the duct 140 or 142 for ventilation is relatively short, and the ventilation loss of the duct 140 or 142 is very small.

In the present embodiment, there is a leakage magnetic flux of the superconducting magnet 21 in the space where the fan motors 110 and 112 are arranged. When the fan motors 110 and 112 are simply arranged in the space where there is a leakage magnetic flux of the superconducting magnet 21, the fan motors 110 and 112 are affected by the leakage magnetic field generated by the superconducting magnet 21. The fan motors 110 and 112 are configured so that the rotors rotate by generating a rotational torque to the rotor based on a change of a magnetic field that the stators generate and the fan connected to the rotor mechanically rotates for ventilation. Due to the influence of the leakage magnetic flux of the superconducting magnet 21, the fan motors 110 and 112 may not operate. Even if they can operate, a rotational torque that generates to the rotors is reduced, which may result in that a desired air volume cannot be obtained.

A magnetic field that the stators of the fan motors 110 and 112 generate is a variable magnetic field always varying to generate a rotational torque to the rotors. The variable magnetic field inversely affects the measurement space of an object. Because it is expected that an MRI apparatus becomes more highly functional, homogenization of a magnetic field in the measurement space should be more highly accurate. The variable magnetic field that the fan motors 110 and 112 generate affects the magnetic field in the measurement space. The undesirable influence to the measurement space depends on the relationship between a direction of the variable magnetic field that the fan motors 110 and 112 generate as well as an orientation and a size of a leakage magnetic field of the superconducting magnet. If the variable magnetic field caused by the fan motors 110 and 112 reaches the imaging space, deterioration is caused in image quality to be measured, which results in a major image quality deterioration problem particularly for SSFP etc. that is high-performance sequence and requires high magnetic field homogeneity.

Figure 2:
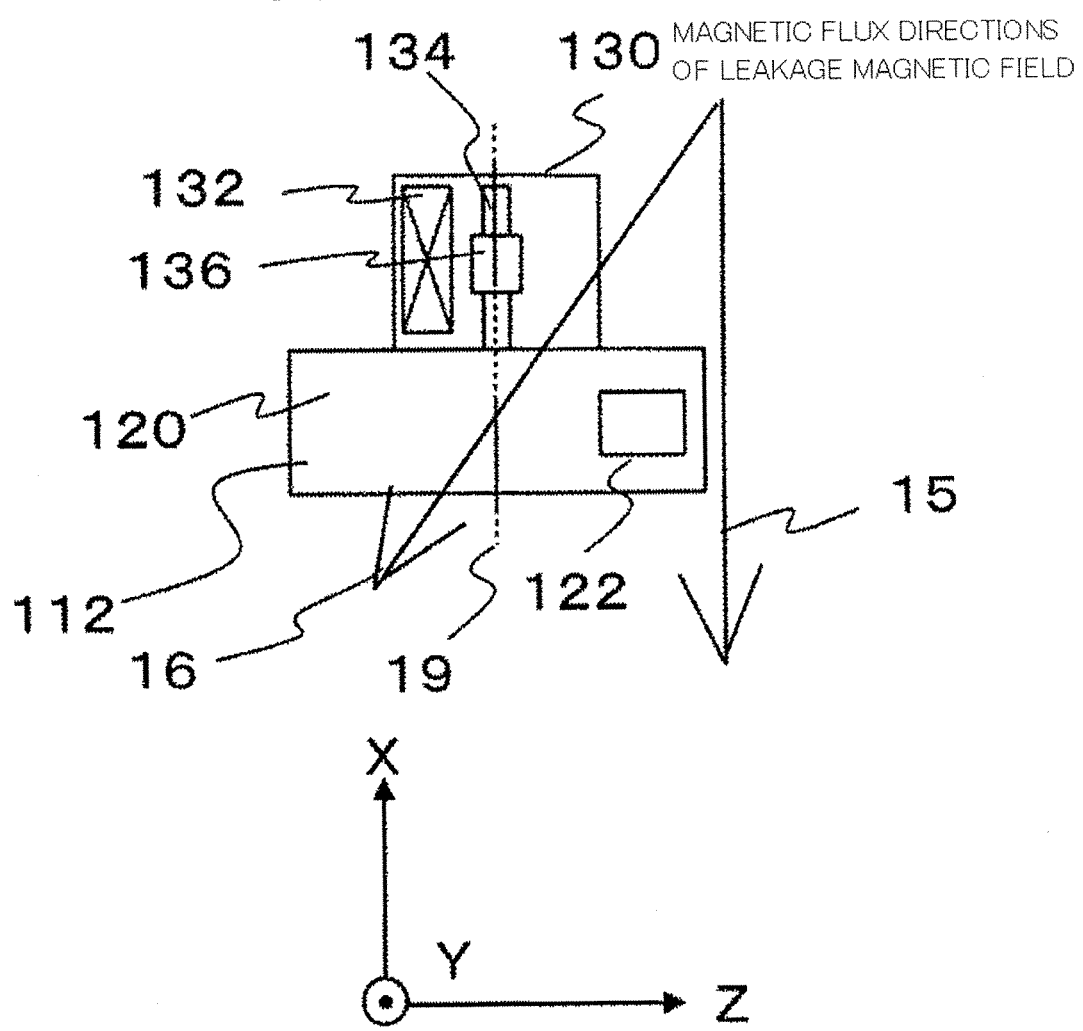
FIG. 2 is an explanatory diagram explaining the leakage magnetic field directions of the superconducting magnet against the fan motor.

FIG. 2 is a diagram showing the structure of the fan motor that shows an example embodiment of the present embodiment and the relationship between the leakage magnetic field directions of the gantry 200 and the arrangement direction of the fan motor. In the present embodiment, the fan motors 110 and 112 using a single-phase AC motor that is inexpensive and has a simple structure are used for ventilating a place in the gantry 200 where cooling is required and particularly in the space where the irradiation coil 38 is arranged and the space 208 where the measurement space is created to accommodate an object. The fan motors 110 and 112 may be a reluctance motor or an AC motor in which a permanent magnet is further provided with the reluctance motor. Also, the fan motors 110 and 112 may be an induction-type motor.

The fan motors 110 and 112 are an AC motor using reluctance as an example and a motor that can operate a plurality of motors by supplying an alternating current voltage of the same frequency to the plurality of motors as described below. The fan motor 110 and the fan motor 112 have the same structure, and hereinafter the fan motor 112 is used as an example to describe the structure.

The fan motor 112 is comprised of the motor unit 130 and the fan unit 120. The motor unit 130 is comprised of a stator as well as a rotor, the rotor has the shaft 134 made of iron that is a magnetic material, and the projection 136 generating a reluctance torque is formed on the shaft 134. Also, the stator includes the stator winding wire 132 wound around the stator core, and the stator winding wire 132 has two winding wires that is connected parallel. A condenser is connected in series to one winding wire, and a phase difference between electric currents flowing in the two winding wires is generated by the condenser. When an alternating current voltage is supplied to the two winding wires connected parallel, an alternative magnetic field acting as a rotating magnetic field that is not a complete rotating magnetic field is applied to the projection 136. A reluctance torque is generated by the projection 136 formed on the shaft 134 and rotates the shaft 134.

The rotation axis of the motor unit 130 is shown as the rotation axis line 19. The rotation axis line 19 corresponds to the length of the shaft 134. The fan unit 120 has a rotating fan (not shown in the diagram) fixed to the shaft 134, takes in air from the rotation axis line 19 direction, leads the taken-in air to the radial direction of the fan by the rotation of the fan that is not shown in the diagram, and then exhausts the air from the ventilation opening 122. The air exhausted from the ventilation opening 122 is lead to the cooling section via the ducts 140 and 142.

The fan motor 112 shown in FIG. 2 is provided in the vicinity of the outside of the superconducting magnet 21 between the outside of the superconducting magnet 21 and the outer cover 202 as shown in FIG. 5 for example. The magnetic flux direction of the leakage magnetic field 15 of the superconducting magnet 21 is an almost X-axis direction in the position passing through the fan motor 112. The rotation axis line 19 of the installed fan motor 112 faces toward the X-axis direction where the magnetic flux direction of the leakage magnetic field 15 is along the rotation axis line 19. Even if a magnetic flux direction of the leakage magnetic field by the superconducting coil 22 is not the magnetic flux direction of the leakage magnetic field 15 but the magnetic flux direction of the leakage magnetic field 16, the gradient of the magnetic flux direction of the leakage magnetic field 16 to the rotation axis line 19 is small and acts as a direction almost along the rotation axis line 19. As described below, when the relationship between the rotation axis line 19 and the magnetic flux direction of the leakage magnetic field of the superconducting magnet 21 is as shown in FIG. 2, an influence of a variable magnetic field generated by the stator winding wire of the fan motor 112 can be reduced. Additionally, it is important that the magnetic flux direction of the leakage magnetic field and the rotation axis line 19 of the fan motor 112 are arranged so that they are not orthogonal to each other as shown in FIG. 2, and it is desirable that they are arranged so that they are parallel to each other as possible.

Figure 3:
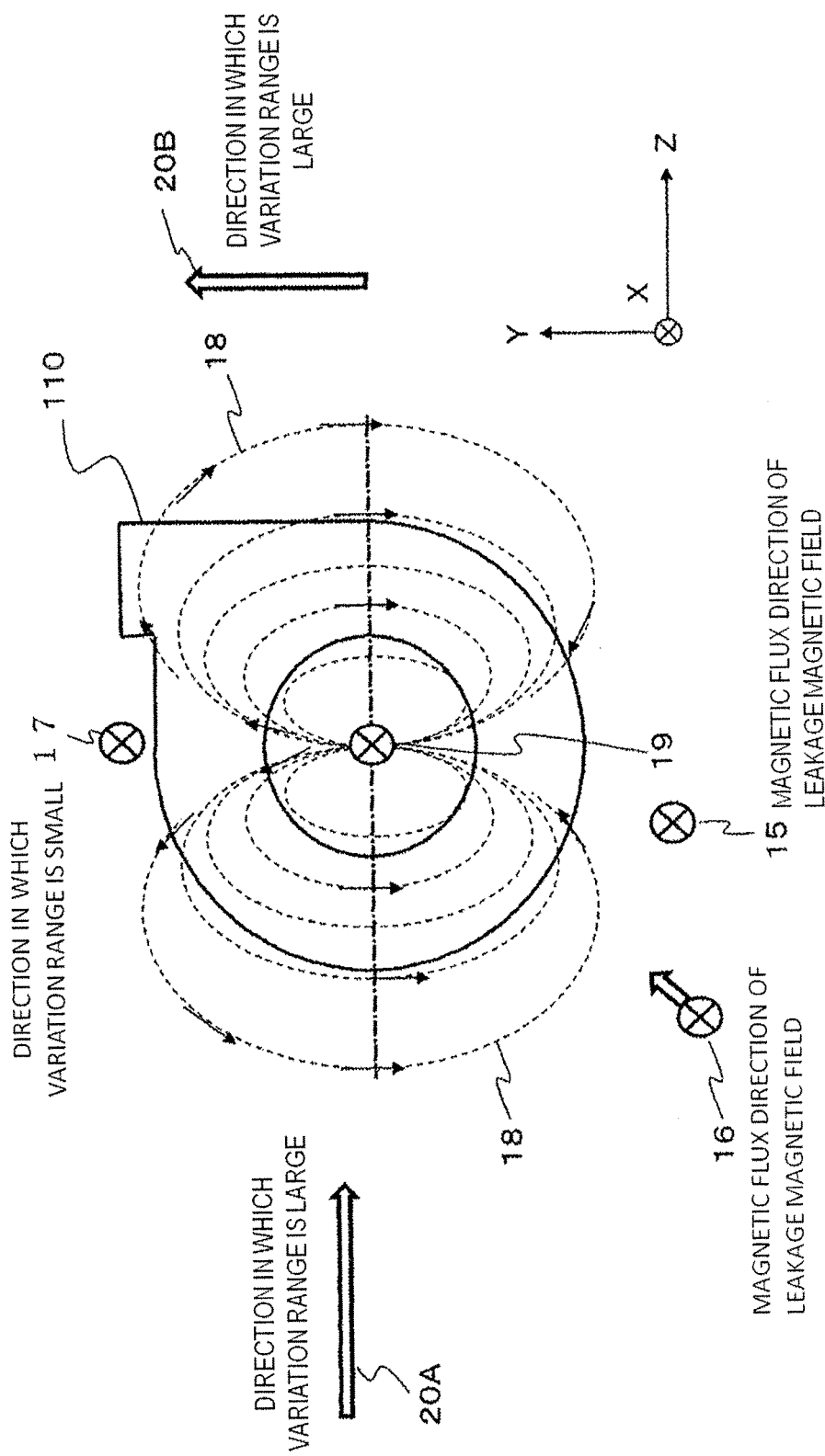
FIG. 3 is an explanatory diagram explaining the leakage magnetic field directions of the superconducting magnet against the variable magnetic field of a fan motor.

FIG. 3 is a diagram showing the directions where the variation range is large 20A and 20B in the variable magnetic field of the fan motor 112 and the direction where the variation range is small 17 in the variable magnetic field. The magnetic fluxes 18 generated by the stator winding wire 132 are switched based on the alternating current to be supplied. Because a single-phase alternating current is supplied to the stator winding wire 132, an excellent rotating magnetic field centered on the rotation axis line 19 cannot be generated differently from a three-phase alternating current being supplied, but a variable magnetic field switching a magnetic field polarity alternately is generated. By switching the magnetic field polarity, a rotational torque is generated to the projection 136 provided on the shaft 134, and the motor unit 130 rotates. Therefore, in the directions where the variation range is large 20A and 20B in the variable magnetic field, a magnetic field direction varies greatly. When magnetic fluxes generated by the superconducting coil 22 of the superconducting magnet 21 are in the directions where the variation range is large 20A and 20B, the magnetic flux 18 generated by the stator winding wire 132 of the motor unit 130 and a magnetic flux generated by the superconducting coil 22 interfere with each other, the motor unit 130 is affected, and then a static magnetic field for measurement to be created by the superconducting coil 22 is also affected. On the other hand, the direction where the variation range is small 17 in the variable magnetic field is a direction along the rotation axis line 19 as well as a direction where there are a few changes of the magnetic flux 18. A change amount of the magnetic flux 18 is small in the direction where the variation range is small 17 in the variable magnetic field, and an absolute value of the magnetic flux density is small, which results in that an influence given to the static magnetic field for measurement is small.

Additionally, the shaft 134 has the projection 136 in the present embodiment and generates a rotational torque by the projection 136. However, this is not limited to the projection 136. By forming a cage-type short circuit sending an induced current based on the variation of the magnetic flux 18 shown in FIG. 3, a rotational torque can be generated. Therefore, not only a reluctance motor but also an induction motor configuration can be used. Also, in order to increase a rotational torque, a permanent magnet may be fixed to the rotor in addition to the projection 136.

As shown in FIG. 3, when a magnetic flux direction of a leakage magnetic field by the superconducting magnet of an MRI is parallel to the rotation axis line 19 of the fan motor 112 as shown in the magnetic flux direction 15 or almost parallel to the rotation axis line 19 of the fan motor 112 as shown in the magnetic flux direction 16, an influence to the fan operation by the leakage magnetic field can be reduced, which can prevent the motor unit 130 from air volume reduction or operation stop by the leakage magnetic field of the superconducting magnet 21. Also, because the variable magnetic field generated by the fan motor at this time is small in the magnetic flux directions 15 and 16 in the leakage magnetic field, an influence to a homogenous static magnetic field for measurement by the motor unit 130 is small. The more the magnetic flux direction in the leakage magnetic field of the superconducting magnet 21 and the rotation axis line 19 direction of the fan motor 112 become parallel, the more the influence of the interference between the motor unit 130 and the superconducting magnet 21 can be used. If the leakage magnetic field and variable magnetic field directions are parallel here, the magnetic flux directions may be mutually inverted.

Figure 4:
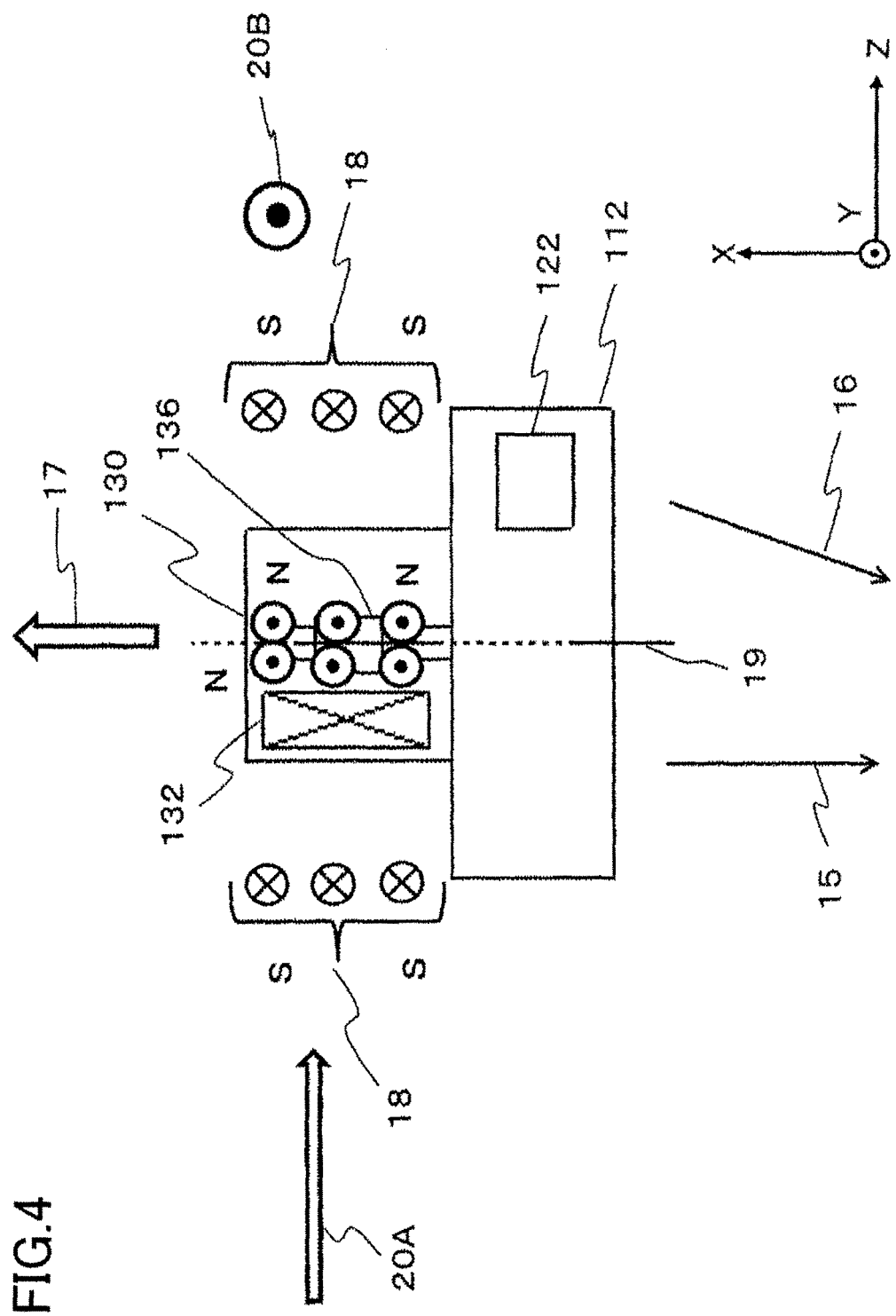
FIG. 4 is an explanatory diagram explaining the leakage magnetic field directions of the superconducting magnet against the orientation of the variable magnetic field of a fan motor.

FIG. 4 is a diagram in which the fan motor 112 shown in FIG. 3 is viewed from the Y direction, i.e. the vertical direction. The magnetic flux 18 generated by the stator winding wire 132 has the N pole on the center side of the motor unit 130, i.e. the rotation axis line 19 side and the S pole on the outer periphery side of the motor unit 130. However, an alternating current is supplied to the stator winding wire 132, and the polarity is inverted by switching the alternating current. Thus, because a polarity of the magnetic flux 18 is always inverted according to the change of the alternating current, magnetic fields in the magnetic flux directions 20A and 20B vary greatly. On the other hand, it is found that the variation is small in the magnetic flux direction 17. Additionally, it is found that the magnetic flux itself generated by the stator winding wire 132 is very small. As described above, it is found that the influence affected by the magnetic flux 18 is small in the magnetic flux directions 15 and 16 in the leakage magnetic field. It is also found that the influence of magnetic fluxes in the magnetic flux directions 15 and 16 in the leakage magnetic field affecting the magnetic field of the stator winding wire 132 inversely is small.

An example in which the leakage magnetic field direction of the superconducting magnet of an MRI apparatus and the orientation of the rotation axis line 19 of the fan motor 112 are arranged so that they are parallel as possible is shown in FIG. 5. FIG. 5, for which a part of the description was already performed, is a part of the cross section of the cylindrical gantry 200 in the long-axis direction (Z-axis direction) and the horizontal direction (X-axis direction). Although there is the superconducting magnet 21 on both sides across the space 208 to accommodate an object, FIG. 5 shows only a half of the superconducting magnet 21 (one side from the longitudinal central axis 23 of the superconducting magnet). In the superconducting magnet 21, a plurality of the superconducting coils 22 are provided so that they are symmetrical with the center axis 24 in the horizontal direction of the superconducting magnet 21. For convenience, only the second superconducting coil 22 is displayed here. A plurality of the superconducting coils 22 are kept in a low temperature by liquid helium in the helium vessel 26. In order to enhance the heat-insulation effect, the radiation shield 27 and the vacuum vessel 28 are provided. The magnetic flux direction 15 in the leakage magnetic field of the magnetic flux created by the superconducting coils 22 radially spreads outward from the space 208 to accommodate an object.

It is desirable that the rotation axis line 19 of the fan motor 112 and the magnetic flux direction 15 in the leakage magnetic field are arranged in a position where they are parallel. For example, if the fan motor 112 is arranged in a position where a magnetic flux direction in a leakage magnetic field is in the X-axis direction, it is desirable that the rotation axis line 19 of the fan motor 112 is arranged so that it faces toward the X-axis direction. Also, if the fan motor 112 is arranged in a position where a magnetic flux direction in a leakage magnetic field is in the Z-axis direction, it is desirable that the rotation axis line 19 of the fan motor 112 is arranged so that it faces toward the Z-axis direction (not shown in the diagram). At this time, the orientation of the rotation axis line 19 of the fan motor 112 may be in either of the positive or negative direction. In the present embodiment, a case in which the fan motor 112 is arranged in a position where a magnetic flux direction in a leakage magnetic field is in the X-axis direction is described.

Although FIG. 6 is a diagram in which the fan motor 112 is provided in almost the same position as FIG. 5, the orientation of the fan motor 112 is different from the state in FIG. 5, which results in that FIG. 6 is a diagram in a case where the fan motor 112 is arranged so that the rotation axis line 19 of the fan motor 112 is orthogonal to the magnetic flux direction 15 in the leakage magnetic field. The rotation axis line 19 of the fan motor 112 faces toward the Y-axis direction, i.e. the vertical direction. Therefore, the magnetic flux direction 15 in the leakage magnetic field from the superconducting magnet 21 almost corresponds to or is close to a direction of a magnetic flux created by the stator winding wire 132. Because of this, the magnetic field created by the superconducting magnet 21 affects the operation of the fan motor 112. Additionally, the variable magnetic field created by the fan motor 112 affects the homogeneity of the static magnetic field created by the superconducting magnet 21. Therefore, it is desirable that the fan motor 112 is installed in the direction described in FIG. 5 (i.e., so that the rotation axis line 19 of the fan motor 112 is parallel to the magnetic flux direction 15 in the leakage magnetic field).

In order to remove the influence of a leakage magnetic field, a method in which the fan motor 112 is shielded with a magnetic material such as iron is considered. However, there are various problems in case of shielding the fan motor 112 with a magnetic material as follows. It is difficult to solve the above problem and a problem to be described below only by shielding the fan motor 112 with a magnetic material. It is desirable that the problem to be described is solved using the above method or the method to be further described below.

Because the fan motor 112 is a consumable that require regular replacement, the following problems occur if it is shielded with a shielding material such as iron. If a shield structure that completely removes an influence only with the shield is used, this results in an impossible operation or a very dangerous operation due to a suction force by the superconducting magnet 21. Alternatively, the magnetic field generating unit of an MRI apparatus needs to be demagnetized to replace the fan motor 112. Also, considering the effects and the price of the fan motor 112, the repeated demagnetization is not financially profitable at all. Therefore, the method to completely shield the fan motor 112 with a magnetic body such as iron is not desirable.

Figure 7:
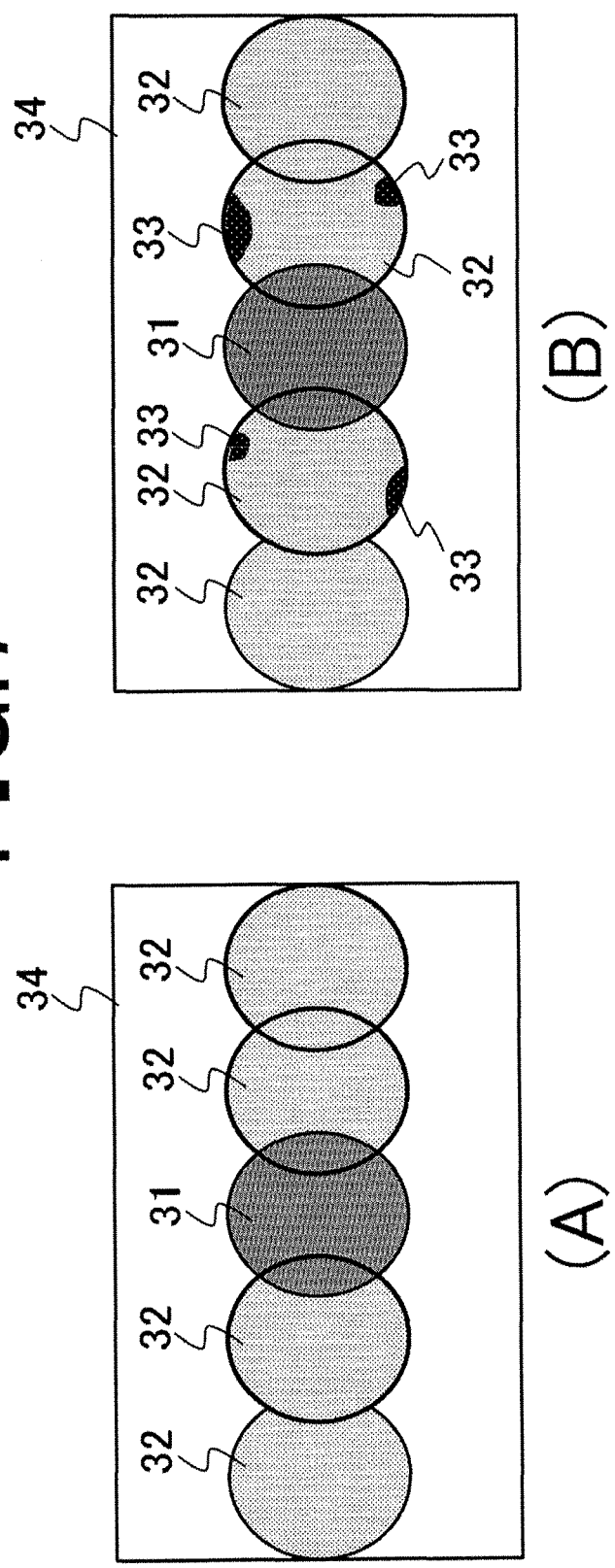
FIG. 7 is a diagram explaining image quality deterioration when the cylindrical phantoms are observed in the axial cross-section.

However, even if the fan motor 112 is arranged so that the leakage magnetic field of the superconducting magnet 21 and the rotation axis line 19 of the fan motor 112 are nearly parallel as described above, it is difficult to reduce an influence of image quality deterioration completely. As performance of an MRI apparatus is further improved in future, this will be a greater problem. FIG. 7 shows an example of the image quality deterioration in case of the SSFP sequence by the variable magnetic field of the fan motor 112 when the fan motor 112 is arranged as shown in FIG. 5.

FIG. 7(A) is an experimental result showing image quality deterioration in a case where the influence of the variable magnetic field by the fan motor 112 affects the imaging space and an image in which a circular phantom is placed and imaged in the imaging space. Originally, only the phantom image 31 should be displayed. However, the influence of the variable magnetic field by the fan motor 112 affects the homogeneity in the static magnetic field in the imaging space, which displays a plurality of the false images 32 with them shifted and superimposed. Particularly, in a case where the fan motors 112 are not arranged in pairs as described below but only one of the fan motor 112 operates as shown in FIG. 5, the image shown in FIG. 7(B) is displayed. In FIGS. 7(A) and 7(B), the symbol 34 shows a field of view (FOV) in the imaging space.

A phantom is placed in the imaging space, and a true phantom image 31 should be displayed on the display screen of the display device 70. However, a plurality of the false images 32 shifted to the phase direction are displayed as shown in FIG. 7(A) in case of being affected by the variable magnetic field of the fan motor 112 or 110 in FIG. 8 to be described later. Additionally, if either one of the fan motor 112 or 110 is operated as shown in FIG. 5, the luminance spots 33 in addition to the false images 32 are displayed as shown in FIG. 7(B). The signal value of the luminance spot 33 is higher than that of the false image 32 in signal strength, which results in more noticeable image quality deterioration.

Such a luminance spot 33 is considered to be created due to the temporal and spatial magnetic field change. That is, by operating only one of the fan motors 112 and 110, the influence of the variable magnetic field appears asymmetrically, which is thought to generate the luminance spots 33. If such luminance spots 33 can be reduced, image quality deterioration can be improved greatly.

Figure 8:
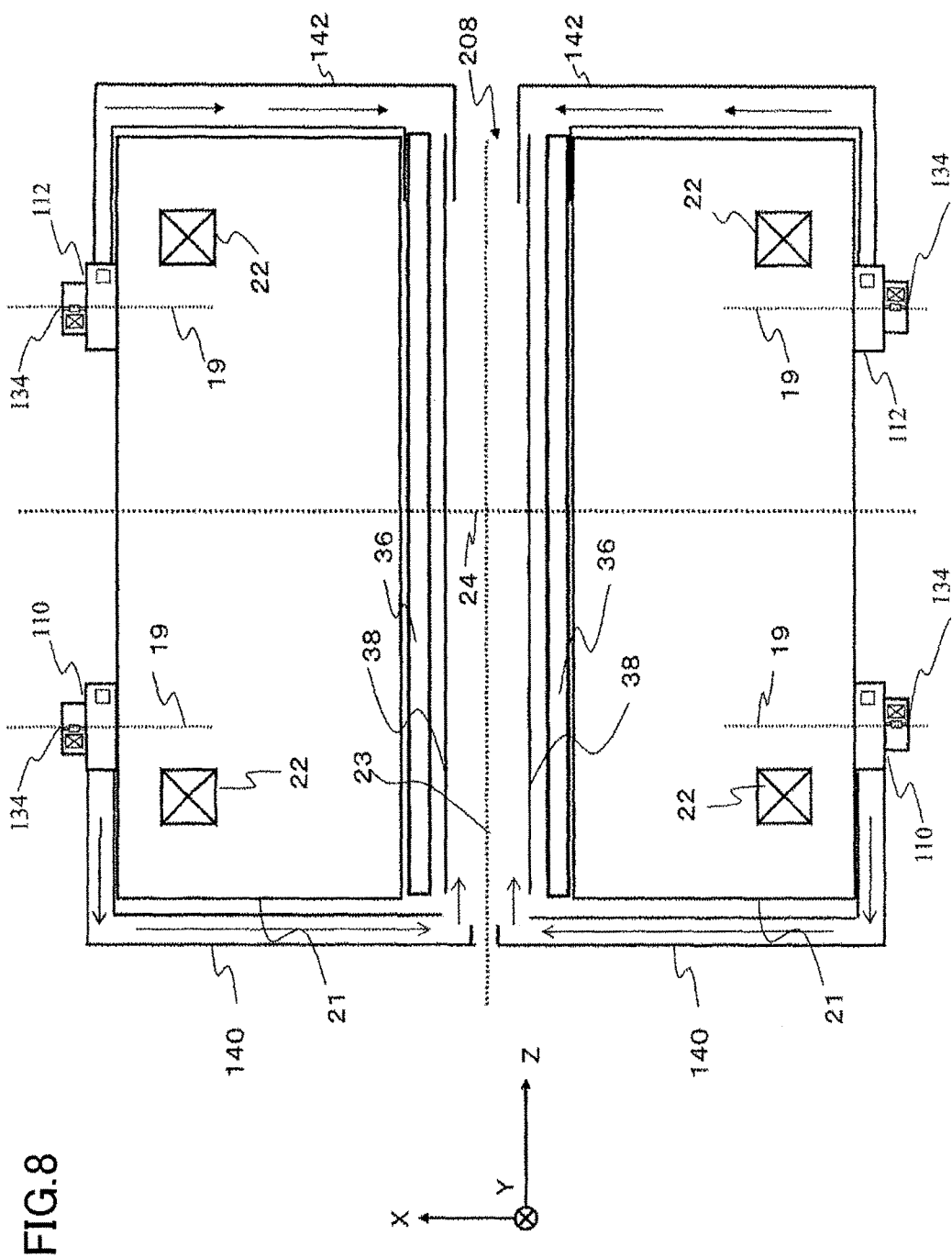
FIG. 8 is a diagram showing the positional relationship between the superconducting magnet and the fan motor.

The embodiment shown in FIG. 8 is an embodiment that can reduce the luminance spots 33. FIG. 8 shows the cross section including the longitudinal central axis 23 of the superconducting magnet. The fan motors 112 are arranged almost symmetrically to the superconducting magnets 21 having a structure symmetrical across the space 208 along the long axis direction of the space 208 and to the longitudinal central axis 23 of the superconducting magnet drawn in the center of the superconducting magnet 21 as shown in the diagram.

The longitudinal central axis 23 of the superconducting magnet is along the Z axis, and a pair of the fan motors 112 is arranged symmetrically to the longitudinal central axis 23 of the superconducting magnet. Additionally, the pair of the fan motors 112 is provided in the vicinity of the outside of the superconducting magnet 21, and the rotation shafts 134 of the respective fan motors 112 are along the X axis. Then, air is sent to the space where the irradiation coil 38 is arranged from the two respective fan motors 112 through the air duct 142. Thus, by arranging a pair of the fan motors 112 almost symmetrically to the longitudinal central axis 23 of the superconducting magnet, the variable magnetic fields influence the static magnetic field almost symmetrically, which can cancel out the mutual influence to some extent. By canceling out the influence of the two fan motors 112 as mentioned above, the luminance spots 33 drawn in FIG. 7(B) can be reduced. Naturally, the air volume from the fan motors 112 is increased compared to a case of the one fan motor, which increases the cooling ability to the irradiation coil 38.

The details for the appropriate arrangement of the fan motor 112 will be described later, but when the number of the fan motors 112 is two as shown in FIG. 8, it is desirable that they are arranged almost symmetrically to the longitudinal central axis 23 of the superconducting magnet 21 or that they are arranged almost symmetrically to the vertical plane passing through the longitudinal central axis 23. However, it is desirable that the leakage magnetic field direction and the shaft 134 are nearly parallel as shown in FIG. 2. Also, it is further desirable that the orientation of the fan motor 112 is arranged almost symmetrically to the longitudinal central axis 23 or the vertical plane passing through the longitudinal central axis 23. Hereinafter, when the fan motors 112 are arranged almost symmetrically to the longitudinal central axis 23 or the vertical plane passing through the longitudinal central axis 23, the orientation of the fan motors will be also arranged almost symmetrically to the longitudinal central axis 23 or the vertical plane.

Also, when a plane that is vertical to the longitudinal central axis 23 and that passes through the center of the longitudinal central axis 23 of the superconducting magnet 21 is defined as the central plane and when the intersection line of the central plane and the cross section of the superconducting magnet 21 is defined as the central axis 24, the other pair of the fan motors 110 is provided across the central axis 24 so that a pair of the fan motors 112 is arranged almost symmetrically to the central axis 24 or the above described central plane. The other pair of the fan motors 110 is arranged almost symmetrically to the longitudinal central axis 23 of the superconducting magnet with each other or almost symmetrically to the vertical plane passing through the longitudinal central axis 23 and adjacently to the outer periphery of the superconducting magnet 21. The respective rotation axis lines 19 of the two fan motors 110 are oriented to the X-axis direction. Thus, by arranging the respective pairs of the fan motors 110 and the fan motors 112 in a state almost symmetrical to the longitudinal central axis 23 of the superconducting magnet or to the vertical plane passing through the longitudinal central axis 23, variable magnetic field influences of the respective fan motors 110 and 112 reaching the imaging space can work so as to cancel out each other, and the signals of the multiple luminance spots 33 appearing on the multiple false images 32 explained in FIG. 7(B) can be reduced, which can prevent the multiple luminance spots 33 from appearing on the image. This results in that image deterioration can be prevented.

As described above, in a case where a plurality of the fan motors 110 and 112 are installed, for example, a pair of the fan motors 112 desirably cools the irradiation coil 38, and the other pair of the fan motors 110 desirably cools the space 208 to accommodate an object. Therefore, it is desirable to configure so that the space where the irradiation coil 38 is provided is cooled by a pair of the fan motors 112 through the respective ducts 142 and the space 208 is cooled by the other pair of the fan motors 110 through the respective ducts 140.

Figure 9:
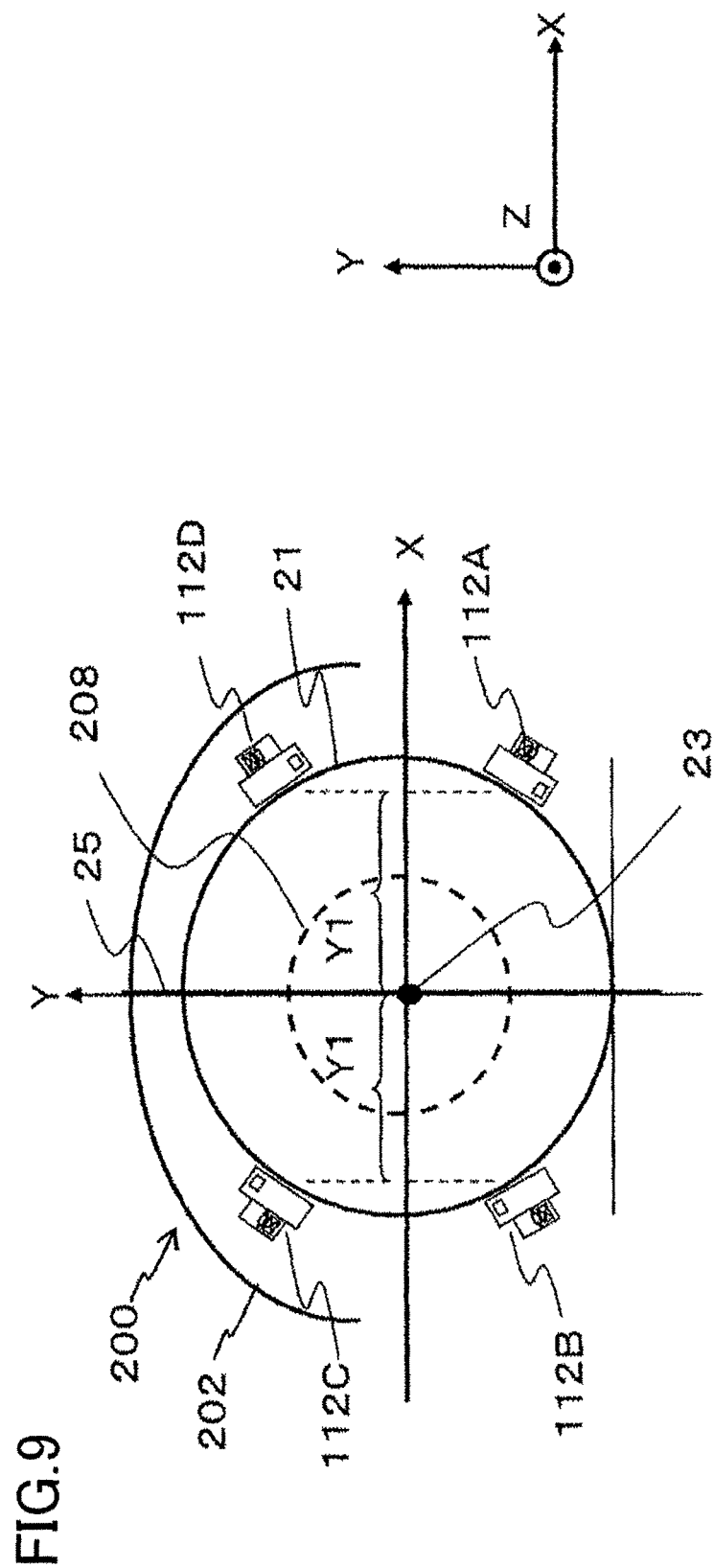
FIG. 9 is a diagram showing the positional relationship between the superconducting magnet and the two fan motors.

FIG. 9 is an explanatory diagram explaining an example of how to arrange a pair of the fan motors 110 or the fan motors 112 to prevent the variable magnetic field influences. FIG. 9 shows the arrangement of the fan motors 112 to the longitudinal central axis 23 of the superconducting magnet 21 of the superconducting coil 22 provided inside the superconducting magnet 21 arranged inside the gantry 200. The longitudinal central axis 23 of the superconducting magnet 21 may be considered as the central axis of the space 208. In order to easily explain the arrangement of the fan motors 112, the symbols of the fan motor 112A to the fan motor 112D are provided as shown in FIG. 9.

The fan motor 112A to the fan motor 112D are arranged so that the respective rotation axis lines (not shown in the diagram) of the fan motor 112A to the fan motor 112D are along the leakage magnetic flux directions of the superconducting magnet 21 respectively.

By arranging the two pairs of the fan motors 112 on the circumference centered on the longitudinal central axis 23 of the superconducting magnet 21 of the superconducting coil 22, adverse influences of specific components from among the adverse influences caused by the variable magnetic field generated by the respective fan motors 112 cancels out each other, which is effective to improve the quality of a constructed MRI image. For example, explaining the fan motor 112A as an example, providing the fan motors 112B, 112C, and 112D is effective to improve the quality of a constructed MRI image.

Additionally, the effect to mutually cancel out the adverse influences of the variable magnetic field generated by the fan motor 112A becomes more remarkable by arranging the fan motor 112A and the fan motor 112B as a pair or arranging them almost symmetrically to the vertical plane passing through the longitudinal central axis 23, by arranging the fan motor 112A and the fan motor 112C as a pair or arranging them almost symmetrically to the longitudinal central axis 23, or by arranging the fan motor 112A and the fan motor 112D as a pair or arranging them almost symmetrically to the horizontal surface (X-Y plane) passing through the longitudinal central axis 23.

Also, in case of centering the fan motor 112D, the effect to mutually cancel out the adverse influences of the variable magnetic field generated by the fan motor 112D becomes more remarkable by arranging the fan motor 112D and the fan motor 112C as a pair or arranging them almost symmetrically to the vertical plane passing through the longitudinal central axis 23, by arranging the fan motor 112D and the fan motor 112B as a pair or arranging them almost symmetrically to the longitudinal central axis 23, or by arranging the fan motor 112D and the fan motor 112A as a pair or arranging them almost symmetrically to the horizontal surface (X-Y plane) passing through the longitudinal central axis 23.

Particularly, in case of arranging the fan motor 112A and the fan motor 112C as a pair or arranging the fan motor 112B and the fan motor 112D as a pair, adverse influences caused by many components from among the adverse influences in a variable magnetic field are mutually canceled out, and this results in a significant effect.

As a result of examination, the fan motors 112 are arranged so that the lengths from the vertical plane 25 displayed along the vertical plane passing through the longitudinal central axis 23 of the superconducting magnet in FIG. 9, i.e. the Y axis to one side and the other side along the X axis are equal, for example, the fan motors are arranged in a position distant by the length Y1 from each other, which can obtain the effect canceling out the adverse influences in the variable magnetic field mutually. Alternatively, by arranging a pair of the fan motors 112 almost plane-symmetrically to the vertical plane 25 or almost line-symmetrically to the longitudinal central axis 23 of the superconducting magnet, the effect in which the adverse influences in the variable magnetic field caused by the fan motors 112 are canceled out mutually is obtained. Although the description is made for the fan motors 112 above, the similar description can be made also for the fan motors 110.

The above effect can be obtained by arranging the fan motors 112 almost line-symmetrically to the longitudinal central axis 23 (Z axis) of the above superconducting magnet or almost plane-symmetrically to the vertical plane passing through the longitudinal central axis 23 of the superconducting magnet. For design and safety, it is desirable that the fan motors 112 are arranged inside the cover 202 of the gantry 200. Also, considering maintenance and inspection for the fan motors and the ducts, it is desirable that they are arranged in the vicinity of the floor where the gantry 200 is placed, such as the positions of the fan motors 112A and 112B in FIG. 9.

Next, the embodiment where there are the four fan motors 112 will be described using FIG. 10. In this case, the arrangement of the fan motors 112 is similar to that in FIG. 8. In case of the four fan motors 112, they are arranged almost symmetrically to the longitudinal central axis 23 in the longitudinal direction of the superconducting magnet 21 or to the vertical plane passing through the longitudinal central axis 23 and almost symmetrically to the central axis 24 in the horizontal direction or to the central plane.

Also, as described above, the rotation axis lines of these four fan motors 112 can prevent an influence of magnetic variation caused by the fan motors 112 by arranging them almost symmetrically to the longitudinal central axis 23 of the superconducting magnet and the central axis 24 in the horizontal direction, which can prevent an influence of the luminance spots 33 on the false images 32. As an application of this, also in a case where the number of the fan motors 112 to be used is a multiple of 4, the luminance spots 33 on the false images 32 can be reduced by arranging according to the similar law.

Figure 10:
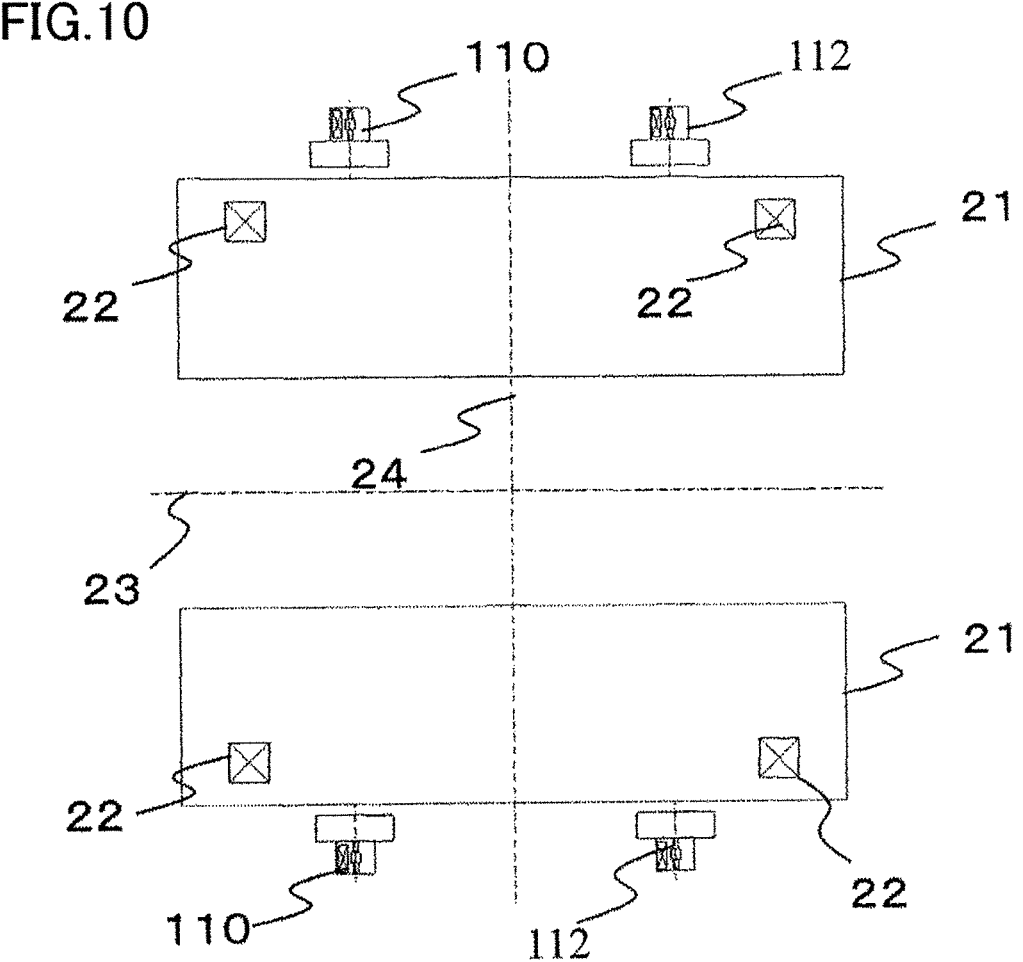
FIG. 10 is a diagram showing the positional relationship between the superconducting magnet and the fan motor.

Although it is described that the fan motors 112 are desirably arranged almost symmetrically to the longitudinal central axis 23 in the longitudinal direction or to the vertical plane passing through the longitudinal central axis 23 and almost symmetrically to the central axis 24 in the horizontal direction or to the central plane in a case where the number of the fan motors 112 to be used is a multiple of 4 in the embodiment of FIG. 10, a case where the number of the fan motors 112 to be used is not a multiple of 4 but a multiple of 2, such as a case of a multiple of 6 for example, will be described.

Figure 11:
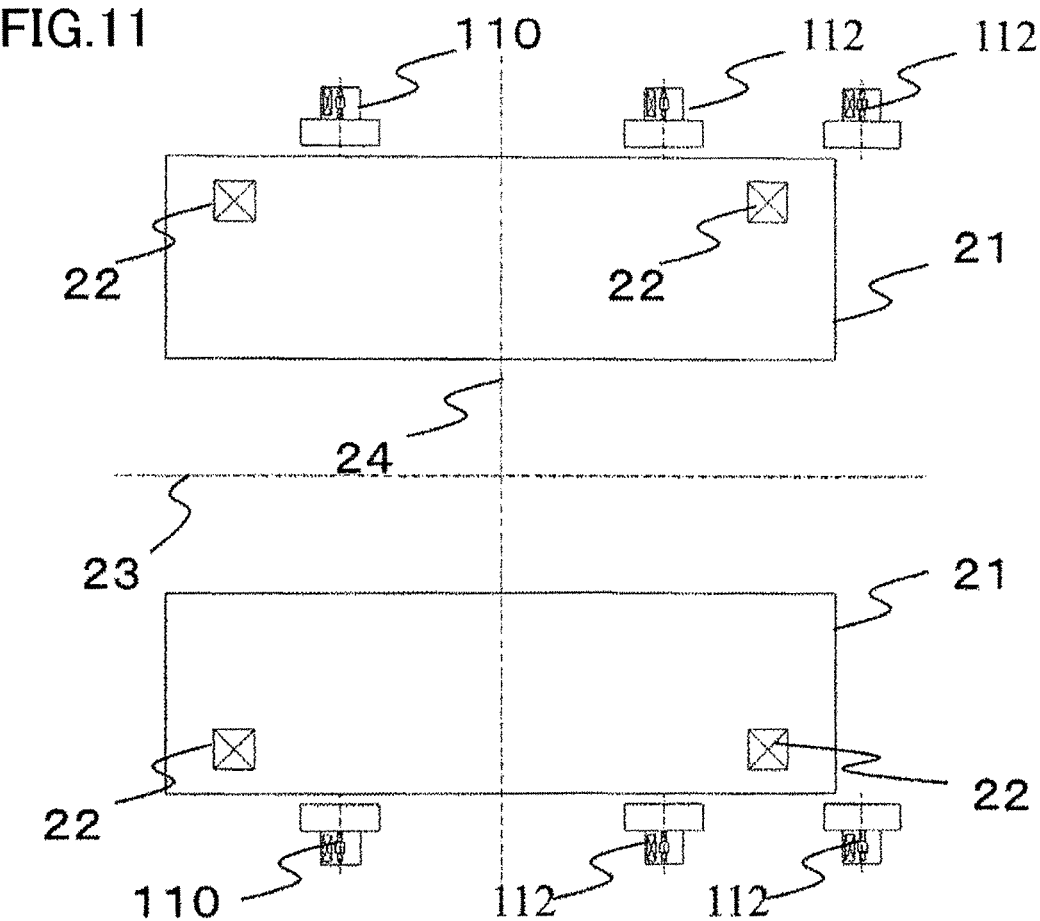
FIG. 11 is a diagram showing the positional relationship between the superconducting magnet and the fan motor.

FIG. 11 is an arrangement example in case of the six fan motors 112. Similarly to FIG. 10, four of the six fan motors 112 are arranged almost symmetrically to the longitudinal central axis 23 in the longitudinal direction or to the vertical plane passing through the longitudinal central axis 23 and almost symmetrically to the central axis 24 in the horizontal direction or to the central plane. The two residual fan motors are arranged similarly to the description about a pair of the fan motors in FIG. 8, and a certain effect can be obtained even if the two fan motors are arranged in arbitrary positions when they are almost symmetrical to the longitudinal central axis 23 in the longitudinal direction or to the vertical plane passing through the longitudinal central axis 23. However, a position where the leakage magnetic field directions 15 and the shafts 134 are nearly parallel is desirable.

As the result of the experiment, in case of arranging the even number of the fan motors 112, first, they are desirably arranged almost symmetrically to the longitudinal central axis 23 in the longitudinal direction or to the vertical plane passing through the longitudinal central axis 23.

Next, they are desirably arranged almost symmetrically also to the central axis 24 in the horizontal direction or to the central plane.

As described above, in a case where the number of the fan motors 112 to be installed is 4×n, the fan motors 112 are desirably arranged almost symmetrically to the longitudinal central axis 23 in the longitudinal direction of the superconducting magnet 21 or to the vertical plane passing through the longitudinal central axis 23 and almost symmetrically to the central axis 24 in the horizontal direction or to the central plane. Also, in a case where the number of the fan motors 112 is 2×(2n−1), 2n pairs of the fan motors 112 are arranged almost symmetrically, in other words, almost symmetrically to the longitudinal central axis 23 in the longitudinal direction or to the vertical plane and almost symmetrically to the central axis 24 in the horizontal direction or to the central plane, and it is desirable that the one residual pair is arranged almost symmetrically to the longitudinal central axis 23 in the longitudinal direction. The luminance spots 33 on the false images 32 can be reduced by arranging in this way.

In case of arranging the four or more fan motors 112, there can be two or more systems such as air-cooling fan motors for an object and the irradiation coil. In this case, at least a pair of the fan motors 112 or the fan motors 110 arranged almost symmetrically to the longitudinal central axis 23 in the longitudinal direction of the superconducting magnet 21 are desirably operated so as to generate the similar magnetic fluxes. By supplying alternating current power to the pair of the fan motors 112 or the fan motors 110 from the common alternating power source, the pair of the fan motors 112 or the fan motors 110 generate the similar magnetic fluxes. In this case, a pair of the fan motors 112 or the fan motors 110 work in directions canceling out variable magnetic fields mutually, and this can reduce an influence in which the luminance spots 33 are displayed.

Figure 12:
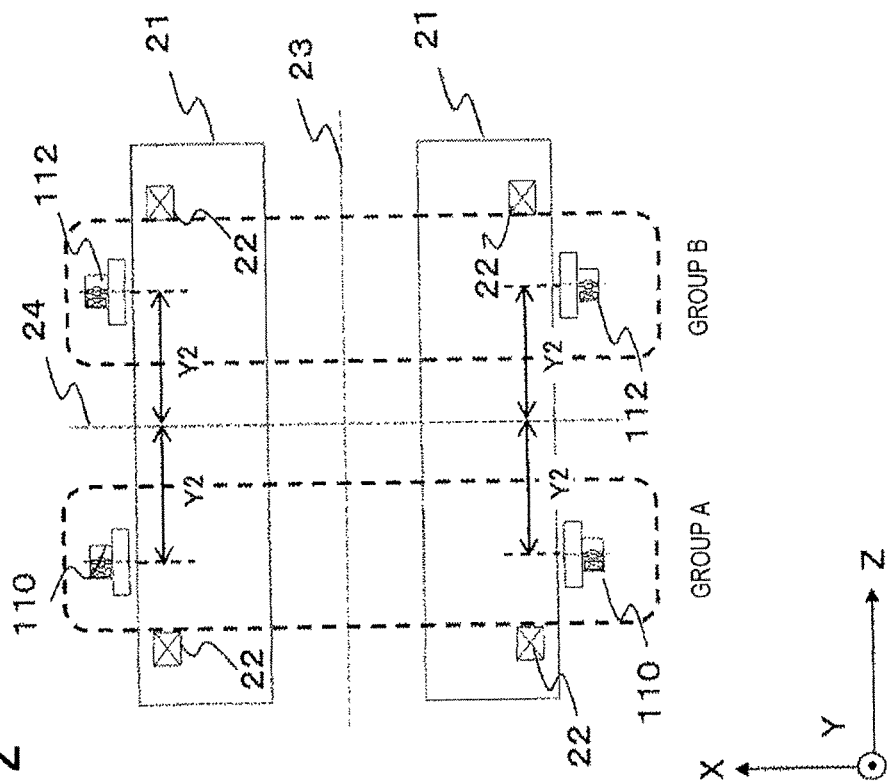
FIG. 12 is a diagram showing the action pattern of the superconducting magnets and the pairs of the fan motors.

The operation patterns in case of arranging the four fan motors 110 or 112 described in FIGS. 8 and 10 as examples will be described using FIG. 12. In FIG. 12(A), a pair of the fan motors 110 and a pair of the fan motors 112 are arranged almost symmetrically to the longitudinal central axis 23 in the longitudinal direction of the superconducting magnet 21, and these are referred to as Group A and Group B respectively. A pair of the fan motors 110 and a pair of the fan motors 112 comprising Group A and Group B are arranged almost symmetrically to the central axis 24 or the central plane, and the distances are Y2.

FIG. 2(B) shows the desirable operation patterns. The operation pattern 1 is a case where both Group A and Group B are operated. Although it is not necessarily needed to supply a common alternating voltage to Group A and Group B at this time, it is desirable that a voltage from a common power source is supplied to the fan motors of each group, i.e. a pair of the fan motors 110 or the other pair of the fan motors 112.

The operation pattern 2 is a case where only the fan motors 112 of Group A are operated, and the operation pattern 3 is a case where only the fan motors 112 of Group B are operated. Therefore, when stopping or starting the fan motor operation, it is desirable to control the operation for each pair of the fan motors, in other words, for each group shown in FIG. 12. When comparing the effects of the operation patterns 1 to 3, the operation pattern 1 operating both Group A and Group B has a greater cooling effect than the other operation patterns 2 and 3 because the number of the fan motors 112 is double, and the effect to reduce the luminance spots 33 on the false images 32 is also great. The effects of the patterns 2 and 3 are almost the same.

Figure 13:
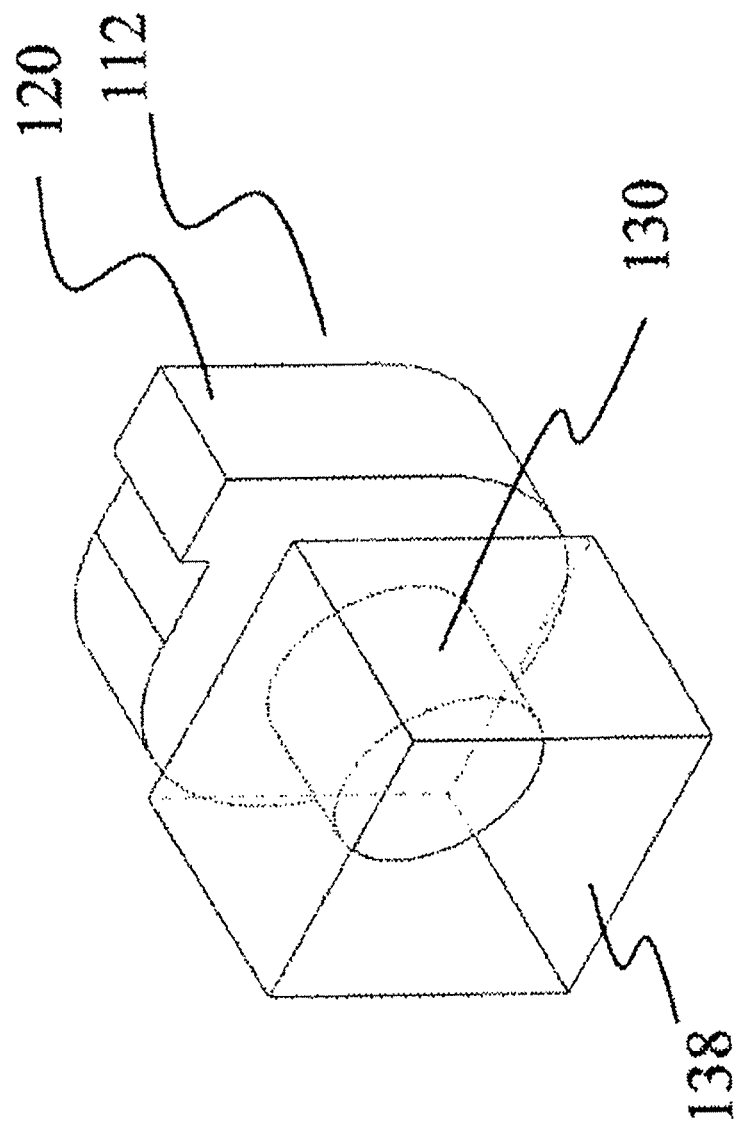
FIG. 13 is a diagram showing the motor shield.

As described above, although the method to reduce influences of variable magnetic fields caused by the fan motors 110 and 112 is described, the method to prevent the influences of variable magnetic fields generated by the fan motors 110 and 112 will be further described using FIG. 13. FIG. 13 is an example of using the conductor cover 138 that covers the motor unit 130 of the fan motor 112 with a plate of a material with small electric resistance, such as a copper plate or an aluminum plate. Because the variable magnetic fields causing image quality deterioration are periodically changed based on a supplied frequency of an alternating power source, magnetic shielding can be performed using an eddy current by covering with a conductor with small electric resistance. An eddy current in a direction where magnetic fluxes are canceled out is always applied to the conductor cover 138 covering the motor unit 130 based on the magnetic flux change by the variable magnetic fields. The smaller the electric resistance the conductor cover 138 has, the larger the eddy current becomes, and this improves the magnetic shielding effect. Also, a copper plate and an aluminum plate are not a magnetic material and does not react to magnetism from the superconducting magnet 21.

Therefore, in addition to the magnetic shielding effect improvement by using a copper plate and an aluminum plate that are a non-magnetic body and have a small resistance value, it is easy to perform maintenance etc. for the fan motors 112 because they are not subject to the magnetic influence of MRI.

Although the motor unit 130 of the fan motor 112 is covered in FIG. 13, the fan motor 112 may be covered entirely. Also, not only the fan motor 112 but also the fan motor 110 may be covered similarly.

As described above, it is desirable that the above fan motor 112 prevents a measurement space from an influence of a variable magnetic field generated by the fan motor 112 as possible. Therefore, it is desirable that multiple pairs of the fan motors 110 or the fan motors 112 can be simultaneously driven by a common alternating power source. As described above, there is a motor having a structure where a rotational torque is generated in a salient pole of a rotor or a permanent magnet provided for a rotor based on periodic polarity change in a magnetic field generated by a stator, and there is a structure where a rotor follows and rotates for a rotational component in a magnetic field generated by a stator in an induction motor using an induced current. This is appropriate for using in a configuration where a plurality of motors are driven from a common alternating power source.

Also, the motor having the above structure can switch a polarity of a magnetic field generated by a stator based on the change of a supplied alternating power source, and a particular switching unit is not required. Therefore, there are a little electrical noise and a small influence on the other devices. When using a DC motor, a commutator etc. that the DC motor has is required. Therefore, electrical noise generated by the DC motor becomes a problem. Additionally, there is a problem that the lifetime of the motor is short. An AC motor does not have such a problem and is suitable. Also, from the viewpoints of control simplification and a power source driving a motor, a single-phase AC motor is the best as a fanning motor.

Also, as a method to prevent image quality deterioration by variable magnetic fields that the fan motors 112 generates, there is a method of changing a frequency of an alternating power source driving the fan motors 112 and driving the fan motors 112 at a frequency with a small influence. When the operating frequency is changed, a frequency of a variable magnetic field to be generated is also changed necessarily. In this case, a higher harmonic component of the variable magnetic field is also changed naturally. Since a frequency component is used as the principle of an MRI apparatus, the generation status of false images also changes.

Figure 14:
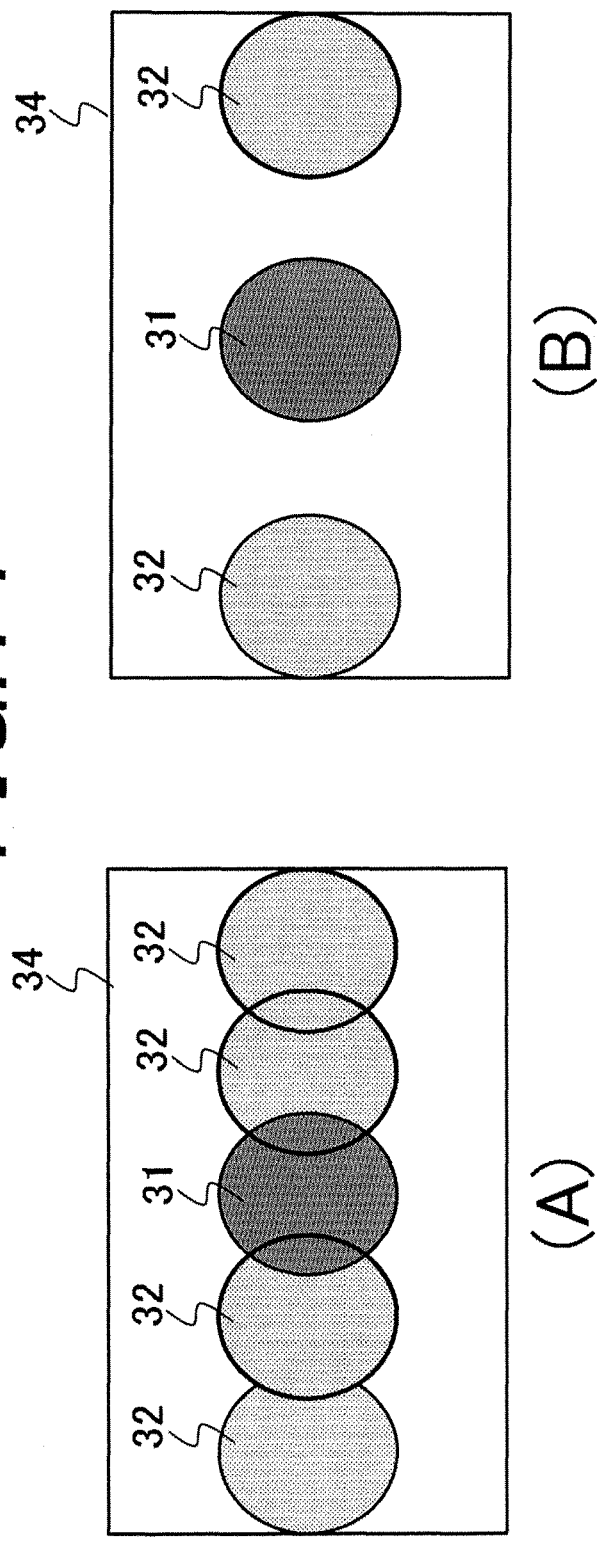
FIG. 14 is a diagram showing image changes after changing a drive frequency of the fan motor.

FIG. 14 shows images in which the cylindrical phantoms are measured in a measurement space similarly to FIG. 7 and the ranges enclosed with the squares show the imaging ranges 34 in the imaging space. FIGS. 14(A) and (B) show examples of image quality deterioration in case of different frequencies. When the frequencies are A in FIG. 14(A) and B in FIG. 14(B), the number of the false images 32 is less and the positions of the false images 32 are remote in case of the frequency B. Thus, the number of the false images 32 and the appearing positions depend on the frequency of an alternating power source driving the fan motors 110 and the fan motors 112. Utilizing this phenomenon, the operation is set to be performed at a frequency where the false images 32 are shifted to the outside of the imaging range 34. Additionally, although a circuit generating alternating current power is needed to set to an arbitrary frequency, for example, alternating current power of an arbitrary frequency can be generated using the inverter 52.

FIG. 15 shows the circuit generating alternating current power of an arbitrary frequency to be supplied to the fan motors 110 and the fan motors 112. In order to generate alternating current power of an arbitrary frequency, direct current power is supplied from the power source 54 to the inverter 52. For example, direct current power can be supplied by commutating alternating current power and storing it in a condenser.

A switching timing of the inverter 52 is controlled by the control unit 56, which can generate alternating current power. The control unit 56 can change a frequency of alternating current power to be generated by changing a switching timing of the inverter 52. By closing the witch 58, alternating current power of the same frequency can be supplied to the fan motors 112 in Group A and the fan motors 110 in Group B. Also, by controlling the switch 58 and the switch 59, the operation patterns explained in FIG. 12(B) can be executed.

FIG. 16 shows the flow chart for calculating a frequency of alternating current power given as a control command to the inverter 52 by computation etc., additionally controlling the switch 58 and the switch 59 by determining the necessity of cooling, and operating or stopping the fan motors 110 and the fan motors 112. Additionally, a process in which known data is stored in the computing concept of this description in advance to search for necessary data is included. For example, the flow chart in FIG. 16 is executed at a certain time interval (Step S1002). Therefore, by changing a frequency of alternating current power generated by the inverter 52, it becomes possible to automatically search an improvement direction while detecting the improvement direction or deterioration direction in the viewpoint of image quality deterioration caused by the appearance of the luminance spots 33 and the false images 32.

A current operating state of the MRI apparatus is detected in Step S1004. In this step, data required to set a frequency of alternating current power and data required to control the switch 58 and the switch 59 are loaded from already input data. Next, in Step S1006, a temperature in a space where the irradiation coil 38 is provided and a temperature in the space 208 where an object is placed are measured. Additionally, in Step S1008, it is determined whether imaging was performed at a frequency of alternating current power that is now being supplied to the fan motors 110 and the fan motors 112, and if imaging was performed, whether the false images 32 and the luminance spots 33 appear on the image and whether the quality of the image is improved or deteriorated about the false images 32 and the luminance spots 33 compared to the previous image.

Based on the information detected in the above Step S1004 and Step S1008, in Step S1010, a computing process is performed to calculate a frequency of alternating current power that reduces a signal strength of the luminance spot 33 and moves the false images 32 to the outside of the imaging range 34 in order to obtain a more desirable frequency of alternating current power. The obtained frequency of alternating current power is temporarily kept. Based on the temperature detected in Step S1006, volumes of air to be blown to a space where the irradiation coil 38 is placed and the space 208 are calculated, and the results are also reflected in the computation in Step S1010. A rotation speed of the motor unit 130 of the fan motor 110 or the fan motor 112 depends on the frequency of alternating current power. Therefore, by increasing a frequency of alternating current power, an air volume of the fan motors 110 or the fan motors 112 can be increased.

In Step S1012, it is determined whether air is blown to a space where the irradiation coil 38 is placed and the space 208 based on the temperature detected in Step S1006. The switch 58 and the switch 59 are controlled to a closed state in case of blowing air to a space where the irradiation coil 38 is placed and the space 208, and the switch 58 and the switch 59 are controlled to an open state in case of stopping air.

Next, a frequency to control the inverter 52 is sent from the control unit 56 to the inverter 52 in Step S1014. Hence, the inverter 52 generates and outputs an alternating current signal based on the sent frequency. Commercial electric power sent from the power source 54 is once converted into a direct current in the inverter 52, and the direct current is converted into alternating current power at a commanded frequency again according to a command value of a frequency from the control unit 56. Thus, operation of the fan motors 110 and the fan motors 112 comprising Group A and Group B is controlled for each of Group A and Group B, and a frequency of alternating current power to be supplied to the fan motors 110 and the fan motors 112 can be optimally controlled. As described above, by controlling the fan motors for each of Group A and Group B, influences of variable magnetic fields generated by the fan motors can be reduced. Also, as explained in FIG. 14, image quality deterioration can be reduced by appropriately determining a frequency of alternating current power to be supplied to the fan motors. The rate of a higher harmonic wave component is high in the variable magnetic fields generated by the fan motors compared to a motor generating a complete rotating magnetic field, and there are many cases where the state of the higher harmonic wave component in the variable magnetic fields generated by the fan motors is changed in a comparatively large scale by changing a frequency of alternating current power to be supplied. Therefore, an effect to reduce image quality deterioration can be expected by changing a frequency of alternating current power to be supplied.

As described above, the MRI apparatus related to the embodiments of the present invention can cool an object efficiently by arranging the fan motors in the vicinity of the superconducting magnet. Also, by optimizing the arrangement of the fan motors, image quality deterioration in a high-functional sequence can be prevented.

DESCRIPTION OF REFERENCE NUMERALS 5 and 16: magnetic flux directions of leakage magnetic field, 17: direction in which variation range in variable magnetic field is small, 18: magnetic flux generated by the stator winding wire 132, 19: rotation axis line, 20A and 20B: direction in which variation range in variable magnetic field is large, 21: superconducting magnet, 22: superconducting coil, 26: helium vessel, 27: radiation shield, 28: vacuum vessel, 30: receiver, 31: phantom image, 32: false image, 33: luminance spot, 33 and 34: imaging range, 36: gradient magnetic field coil, 38: irradiation coil, 50: table, 52: inverter, 54: power source, 56: control unit, 58 and 59: switch, 60: control processor, 70: display device, 80: input/output device, 100: MRI apparatus, 112: fan motor, 120: fan unit, 122: ventilation opening, 130: motor unit, 132: stator winding wire, 134: shaft, 136: projection, 138: conductor cover, 140 and 142: duct, 200: gantry, 202 and 206: cover, 204: portion in which cover is removed, 208: space

The invention claimed is:

1. A magnetic resonance imaging apparatus having:
a gantry comprising a static magnetic field generating magnet having a cylindrical space to accommodate an object for generating a static magnetic field in the said space;
a gradient magnetic field generating coil for generating a gradient magnetic field; and
an irradiation coil for irradiating a high-frequency signal, a table for placing the object, and an input/output device including a display device,
wherein at least a pair of cooling fan motors arranged almost symmetrically to the central axis, the central axis extending along the long-axis direction of the cylindrical space and located in the center in a horizontal direction of the static magnetic field generating magnet or a vertical plane passing through the central axis is provided,
wherein each cooling fan motor that comprises the at least a pair of cooling fan motors is installed so that a rotation axis line faces toward a direction almost along a leakage magnetic flux that the static magnetic field generating magnet generates,
wherein the static magnetic field generating magnet includes a superconducting magnet, the gantry includes an outer cover, and the at least a pair of cooling fan motors is on the outside of the superconducting magnet and is installed inside the outer cover,
wherein each cooling fan motor that comprises the at least a pair of cooling fan motors includes a fan unit blowing air by an alternating current motor and rotation of the alternating current motor, and the alternating current motor has a stator winding wire generating a variable magnetic field based on an alternating current, and an alternating current power supplying unit supplying the alternating current is provided, and the alternating current supplied from the alternating current power supplying unit is supplied to each stator winding wire of the respective cooling fan motors comprising the at least a pair of cooling fan motors,
wherein a control unit commanding a frequency of the alternating current to be supplied to the respective at least a pair of cooling fan motors is provided, the alternating current power supplying unit has an alternating current power generation device generating alternating current power, and an alternating current of a frequency based on a command from the control unit is supplied to the respective cooling fan motors from the alternating current power generation device, and
wherein the control unit is configured to calculate a frequency of alternating current power that reduces image quality deterioration due to an influence of variable magnetic fields generated by the respective cooling fan motors comprising the pair based on input information and send the calculated frequency of alternating current power as a command to the alternating current power generation device, and the alternating current power generation device generates alternating current power of the commanded frequency and supplies it to the respective cooling fan motors.

2. The magnetic resonance imaging apparatus according to claim 1, wherein the at least a pair of cooling fan motors is installed nearer to a floor side than the cylindrical space to accommodate the object.

3. The magnetic resonance imaging apparatus according to claim 1, wherein each cooling fan motor that comprises the at least a pair of cooling fan motors includes a fan unit blowing air by an alternating current motor and rotation of the alternating current motor, and the alternating current motor includes a stator winding wire generating a variable magnetic field based on the supplied alternating current, the cooling fan motor has a conductor cover made of a conductor plate, and the alternating current motor is at least covered with the conductor cover.

4. The magnetic resonance imaging apparatus according to claim 3, wherein the conductor cover at least covering the alternating current motor is made of a non-magnetic metal.

5. A magnetic resonance imaging apparatus having:
   a gantry comprising a static magnetic field generating magnet having a cylindrical space to accommodate an object for generating a static magnetic field in the said space;
   a gradient magnetic field generating coil for generating a gradient magnetic field; and
   an irradiation coil for irradiating a high-frequency signal, a table for placing the object, and an input/output device including a display device,
   wherein at least two pairs of cooling fan motors, including a first pair and a second pair, are arranged almost symmetrically to a central axis, the central axis extending along a long-axis direction of the cylindrical space and located in a center in a horizontal direction of the static magnetic field generating magnet or a vertical plane passing through the central axis is provided,
   wherein the at least two pairs of cooling fan motors including the first pair and the second pair are installed, and in case of defining the central axis that extends along the long-axis direction of the cylindrical space as the first central axis, the central axis of the static magnetic field generating magnet extending in the horizontal direction across the first central axis as the second axis, a vertical plane passing through the first central axis extending in the vertical direction as the first vertical plane, and a vertical plane passing through the second central axis extending in the vertical direction as the second vertical plane, each cooling fan motor comprising the first pair and each cooling fan motor comprising the second pair are arranged almost symmetrically to the second central axis and the second vertical plane.

* * * * *